(12) United States Patent
Shaw

(10) Patent No.: US 9,581,591 B2
(45) Date of Patent: Feb. 28, 2017

(54) SYSTEMS AND METHODS FOR MEDICAL DATA PROCESSING AND ANALYSIS

(75) Inventor: Andrew Mark Shaw, Exeter (GB)

(73) Assignee: UNIVERSITY OF EXETER, Devon (GB)

( * ) Notice: Subject to any disclaimer, the term of this patent is extended or adjusted under 35 U.S.C. 154(b) by 686 days.

(21) Appl. No.: 13/809,288

(22) PCT Filed: Jul. 15, 2011

(86) PCT No.: PCT/GB2011/051335
§ 371 (c)(1),
(2), (4) Date: Feb. 19, 2013

(87) PCT Pub. No.: WO2012/010871
PCT Pub. Date: Jan. 26, 2012

(65) Prior Publication Data
US 2013/0166219 A1    Jun. 27, 2013

(30) Foreign Application Priority Data
Jul. 23, 2010   (GB) .................................. 1012376.8

(51) Int. Cl.
G01N 33/48      (2006.01)
G01N 33/543     (2006.01)
G06F 19/00      (2011.01)
G01N 33/564     (2006.01)
G06F 19/18      (2011.01)

(52) U.S. Cl.
CPC ..... *G01N 33/54373* (2013.01); *G01N 33/564* (2013.01); *G06F 19/34* (2013.01); *G06F 19/3437* (2013.01); *G01N 2333/4716* (2013.01); *G01N 2333/4724* (2013.01); *G01N 2800/52* (2013.01); *G06F 19/18* (2013.01)

(58) Field of Classification Search
CPC ............................................... G01N 33/54373
USPC ........................................................ 702/19
See application file for complete search history.

(56) References Cited

U.S. PATENT DOCUMENTS

2009/0062624 A1    3/2009  Neville

FOREIGN PATENT DOCUMENTS

| WO | 03/084388 | 10/2003 |
| WO | 2008117086 | 10/2008 |
| WO | 2008117087 | 10/2008 |
| WO | 2009056875 | 5/2009 |

OTHER PUBLICATIONS

International Search Report and Written Opinion for PCT/GB2011/051335 dated Jan. 18, 2012.
Search Report for GB 1012376.8 dated Oct. 17, 2011.
"Plasma concentartion of procalcitonin and systemic inflammatory response syndrome after colorectal surgery"; Acta Anaesthes, Scand., vol. 49, 2005, Sarbinowski, R. et al., pp. 191-196.
"Complement activation during cardiopulmonary bypass in infants and children"; J. Thoracic Cardiovasc. Surg., vol. 106, 1993, Seghaye, M.C., et al.; pp. 978-987.
"Complement activity and pharmacological inhibition in cardiovascular disease"; Can. J. Cardiol., vol. 22, Suppl. B, 2006; Theroux, P. et al., pp. 18B-24B.
"Complement Activation in Coronary Artery Bypass Grafting Patients Without Cardiopulmonary Bypass"; Chest, vol. 116, 1999, Gu, Y.J. et al., pp. 892-898.
"Inflammatory response in an immunosuppressed patient with Wegener's granulomatosis"; Perfusion, vol. 19, 2004, Mirsadraee, S. et al., pp. 127-131.
International Preliminary Report on Patentability dated Jan. 23, 2013 in Application No. PCT/GB2011/051335.

*Primary Examiner* — Jerry Lin
(74) *Attorney, Agent, or Firm* — Snell & Wilmer L.L.P.

(57) ABSTRACT

We describe a system/method for predicting the outcome of a medical procedure on a patient. The system/method uses using complement cascade data representing levels of a set of complement cascade markers in the patient at a succession of peri-operative time intervals, determining deviations from a model of the response to provide a pre-symptomatic prediction of the outcome. In embodiments the complement cascade pathways include the lytic pathway and at least one of the lectin pathway, the classical pathway and the alternative pathway, and the biomarkers include at least C3. The system may include an electroluminescence or plasmon-resonance multianalyte detector to analyze a blood sample from the patient.

7 Claims, 11 Drawing Sheets

SYSTEMS AND METHODS FOR MEDICAL DATA PROCESSING AND ANALYSIS

CROSS-REFERENCE TO RELATED APPLICATIONS

This application is a U.S. national phase filing under 35 U.S.C. §371 of PCT/GB2011/051335 filed Jul. 15, 2011, which is incorporated by reference in its entirety.

FIELD OF THE INVENTION

This invention relates to systems, methods and computer program code for capturing and processing human (or animal) immune system data to predict the outcome of a medical procedure, in particular surgery.

BACKGROUND TO THE INVENTION

We have previously described, for example in WO2008/117087, WO2008/117086 and WO2009/056875, techniques for employing plasmon resonance based sensing in photonic biosensor arrays to provide extremely sensitive assay of multiple biological analytes in parallel. Embodiments of these techniques may be employed to analyse, for example, blood serum to detect target analytes to nanogram, potentially down to attogram levels.

The inventor has recognised that systems of this type, and also other multianalyte detectors/platform assay devices, may advantageously be employed to detect components of the complement system, that is the biochemical cascade that is part of the (innate) immune system response.

Broadly speaking there are three main pathways of complement activation, the classical pathway (CP), the alternative pathway (AP) and the lectin pathway (LP). These converge on or link to C3 convertase activation (and also C5 convertase activation), and this in turn leads to a lytic pathway which eventually forms a membrane attack complex (MAC). FIG. 1 shows the Complement Cascade, showing the Classical, Lectin and Alternative activation pathways leading to the Lytic pathway.

The inventor has conducted a program of research into the response of the complement cascade to a surgical insult, with surprising results.

SUMMARY OF THE INVENTION

According to a first aspect of the present invention there is therefore provided a method of predicting the outcome of a medical procedure on a patient, the method comprising: inputting patient complement cascade data comprising data representing levels of a set of complement cascade markers in said patient at a succession of time intervals following said medical procedure, wherein said patient complement cascade data defines a patient recovery pathway representing an evolution over time of a complement cascade in said patient; comparing said patient recovery pathway represented by said patient complement cascade data with at least one corresponding cohort recovery pathway defined by cohort complement cascade data representing an evolution over time of a complement cascade in a cohort of patients, to determine a deviation between said patient recovery pathway and said cohort recovery pathway; determining a predicted outcome of said medical procedure responsive to said determined deviation.

In some preferred embodiments of the technique the deviation is determined by determining a score for the patient recovery pathway representing a deviation of this from the cohort recovery pathway. In embodiments this score is determined at a plurality of different times, conveniently corresponding to the times at which the complement cascade markers are sampled, and a weighting is applied dependent on the confidence limit of the cohort recovery pathway, for example depending upon the deviation from a 95% confidence limit of the cohort recovery pathway. Additionally or alternatively other metrics may be employed including, but not limited to: the respective shapes of the pathways over corresponding time intervals, a slope at one or more points on a pathway, a maximum, minimum or turning point value on a pathway, and an area above or below a curve defined by a pathway.

In embodiments of the method the cohort recovery pathway defines a Bayesian prior probability and the procedure determines a Bayesian likelihood (conditional probability) of the predicted outcome given the patient recovery pathway. In embodiments the prior probability may be defined by a level of just a single marker, or a combination of markers. Broadly speaking the cohort defines the recovery curve for a set of key parameters and deviations from this are calculated with Bayes' probability rule to determine a predicted outcome.

In embodiments a prediction is made responsive to a set of complement cascade marker levels measured over an initial time interval of less than 24 hours, or less than 18 hours, from the medical procedure, for example a surgical insult. Preferably in embodiments the levels of the complement cascade markers are normalised, for example using levels determined prior to the medical procedure. Although a mathematical analysis of the data is convenient for implementation in software, in embodiments a nomogram may additionally or alternatively be provided for predicting the procedure outcome. In embodiments a patient or cohort recovery pathway may be defined by a mathematical combination or ratio of levels of a plurality of the complement cascade markers.

In some preferred embodiments of the technique a plurality of patient recovery pathways is compared to a corresponding set of cohort recovery pathways, for example representing fluxes in different complement cascade pathways (classical/alternative/lectin) and the predicted outcome may then be determined in response to the set of deviations, more particularly to a determined level of differential activations of the different complement cascade pathways (or combinations of pathways).

In embodiments of the method the predicted outcome includes differentiating between one or more of: normal recovery, infection, sepsis, a Gram negative bacterial infection, a Gram positive bacterial infection, a viral infection, and a fungal infection. Additionally or alternatively the predicted outcome may include classifying the patient into one or more categories having different expected outcomes for recovery.

In embodiments a marker for the alternative pathway may include C3 and/or factor B, more particularly Bb and/or C3dg. A marker for the classical/lectin pathways may include C2 or C4, more particularly C4d. Additionally or alternatively a differential flux between one or more of these activation pathways and a terminal pathway may be determined; a marker for the terminal pathway may include one oar more of C5, C6, C7, C8 and C9. Additionally or alternatively a complement cascade marker may comprise a CC fragment. Monitoring the level of a CC fragment has the advantage that the data is more intuitive in that the level of a fragment, say a C3 or C4 fragment, will generally rise as the "parent" is consumed, and it is easier to detect a rising level from a baseline than a falling level from an initially normalised value.

Embodiments of the method may additionally or alternatively employ a fragment from a complement protein, for example to compensate or correct for changes in a fluid level of the patient and/or as a proxy for the protein prior to fragmentation.

It is particularly advantageous in embodiments of the method to determine the levels of the complement cascade markers substantially in parallel—that is substantially simultaneously: this gives the best answer for the CC levels, which can otherwise change with respect to one another during the analysis. For similar reasons it is also advantageous to measure the CC levels "actuely", that is in the general vicinity of the patient so that the measurement can be made within 1 hour, preferably within 30 minutes of a blood sample being taken.

Embodiments of the above described methods are particularly useful for pre-symptomatic predictions, and for suggesting a differential diagnosis.

In embodiments of the method the levels of the complement cascade markers are characteristic of the degree of activation of a set of complement cascade pathways including the lytic pathway and at least one of the lectin pathway, classical pathway and alternative pathway. The determining of the deviation from the cohort may then be made using model data defining a model having at least levels of markers of these pathways to predict the outcome from a set of outcomes including, in embodiments at least recovery of and infection of the patient. In embodiments the pathways include at least two of the lectin pathway, the classical pathway and the alternative pathway and the model is used to predict the outcome by differentiating between different types of causes of infection responsive to the determined levels of activation of the different complement cascade pathways.

More particularly the model may comprise a representation of fluxes of complement components on the complement cascade pathways. The method then may determine probability data through the different types of infection dependent on the fluxes of the complement components in these pathways. In embodiments the fluxes comprise at least two of $J_A$, $J_C$, and $J_L$, representing the fluxes in, respectively, the alternative, classical and lectin pathways. Then the probability for the different types of infection may be determined by identifying greater than a threshold probability of one or more of:

$J_A+J_L>J_C$ $J_A>J_L+J_C$ $J_A>J_C+J_L$ $J_A+J_L>J_C$ $J_C>J_A+J_L$.

In a related aspect the invention provides a medical procedure outcome prediction system, the system comprising: working memory; program memory; a processor coupled to said working memory and to said program memory; an input to receive patient complement cascade data comprising data representing levels of set of complement cascade markers in said patient at a succession of time intervals following said medical procedure, wherein said patient complement cascade data defines a patient recovery pathway representing an evolution over time of a complement cascade in said patient; and wherein said program memory stores processor control code to: compare said patient recovery pathway represented by said patient complement cascade data with at least one corresponding cohort recovery pathway defined by cohort complement cascade data representing an evolution over time of a complement cascade in a cohort of patients to determine a deviation between said patient recovery pathway and said cohort recovery pathway; and determine a predicted outcome of said medical procedure responsive to said determined deviation.

In some preferred embodiments the system also includes a multianalyte detector to analyse a sample of blood from the patient to determine concentration data for the markers of a set of complement cascade pathways including the lytic pathway, and at least one of the lectin pathway, the classical pathway, and the alternative pathway.

Analytical Systems

Thus the invention also provides a system for indicating the response of a patient to surgery, the system comprising: a multianalyte detector to analyse a sample of blood from said patient to determine, substantially in parallel, absolute concentration data for each of a set of biomarkers of a set of complement cascade pathways, wherein said complement cascade pathways include the lytic pathway and at least one of the lectin pathway, the classical pathway and the alternative pathway; a data analyser, coupled to said multianalyte detector, to receive and analyse said absolute concentration data, wherein said data analyser stores model data defining a model having at least absolute concentrations of said biomarkers as parameters, and wherein said data analyser is configured to process said absolute concentration data using said model data to determine probability data representing a likelihood of one or more outcomes of said surgery, wherein said outcomes include at least a determined or threshold level of recovery of said patient and a determined or threshold level of infection of said patient; and an output device, coupled to said data analyser, to provide to a user an indication of a said outcome dependent on said determined probability data.

The inventor has recognised that by predicting whether/when a patient recovers from surgery, a substantial fraction of patients may be released from hospital early as compared with a default length of stay, hence saving a substantial amount of money. The inventor has further recognised that an arrangement as described above is able to make a prediction on which, for example, a decision regarding early release may be based. In addition in embodiments the same system may also be employed to predict infection and/or sepsis. Preferably the biomarkers include at least C3 and/or C5.

In some preferred embodiments the multianalyte detector comprises a surface plasmon resonance-based biosensor array comprising a transparent substrate bearing a plurality of electrically conductive assay regions (for example as described in WO2008/117087), which facilitates identification of biomarkers with a small volume of blood, for example, less than one ml, and provides a rapid response which facilitates use, for example, in theatre. More particularly in embodiments the multianalyte detector is configured to determine the concentration data within a time duration of no greater than 60, 30, 15, 10 or 5 minutes. This is particularly advantageous as it facilitates determining a concentration of C3 prior to hydrolysis into peptide fragments C3a and C3b.

In some preferred embodiments a set of biomarkers includes complement components and also regulators/inhibitors of the complement cascade, preferably between 10 and 50 components. In embodiments the system determines the flux or activation level of the CP, AP and LP, as well as the lytic pathway, and uses this data to monitor a predicted level of infection as compared with an increased flux in the lytic pathway arising from the initial surgical insult (knife/bleeding). In some preferred embodiments the data analyser is configured to determine the probability data for different types of infection dependent on the determined fluxes in the different pathways, for example to differentiate between antibodies/viral infection/bacteria (optionally either Gram-positive or Gram-negative)/C-reactive protein (CRP)/fungal infection/other. In some preferred embodiments the data analysis system determines a level of infection to identify the predicted onset of sepsis.

Preferably a time series of concentration data is captured and employed in the data analysis since a set of concentration values at a single time may be 'degenerate' in that they may define a plurality of different potential outcomes of the patient. Thus, for example, the inflammation/tissue repair resulting from the initial surgical insult can be differentiated from an infection response in particular after a number of hours when healing starts. Samples may be taken at one or more of: before surgery; at/during surgery; at the point of 'close-up'; at four hour intervals thereafter until, say, 12 hours, then at 12 hour intervals, and so forth.

In embodiments relative concentrations are also determined and used in the data analysis, for example to differentiate infection from a background immune process such as might be caused by arthritis. Optionally the model may be stratified into groups of patients who respond similarly within a group but differently between groups.

The model data may be determined from and/or updated in response to continuing use of the system, for example to take account of actual outcomes/survival times, to update error bars on probabilities/likelihoods, to classify groups of patient responses, to better determine parameters, for example one or more rate constants, and the like.

In one implementation the system comprises a first apparatus embodying the multianalyte detector, and including a first processor, coupled via a computer network to a database/data analyser as described above which stores a time series of patient data, including historical data, and which performs the analysis. In embodiments the results may be returned to the first apparatus and output, for example on a screen or hardcopy to provide a predicted indicator of outcome of the procedure. This may be employed to determine whether to schedule a patient for early release or to keep a patient under close observation. It will be appreciated that whilst the above described system provides an indication which may be useful, for example, for scheduling occupancy of hospital beds, it does not provide a clinical diagnosis or qualified medical opinion on a patient.

In a related further aspect the invention provides a carrier medium carrying processor control code for indicating the response of a patient to surgery, the code comprising code to: receive concentration data from a multianalyte detector, said concentration data defining concentrations of each of a set of biomarkers of a set of complement cascade pathways, wherein said complement cascade pathways include the lytic pathway and at least one of the lectin pathway, classical pathway and the alternative pathway; analyse said concentration data using model data, said model data defining a model having at least concentration of said biomarkers as parameters; and wherein said analysis comprises processing said concentration data using said model data to determine probability data representing a likelihood of one or more outcomes of said surgery, wherein said outcomes include at least a determined or threshold level of recovery of said patient and a determined or threshold level of infection of said patient; and output to a user an indication of a said outcome dependent on said determined probability data.

The invention further provides processor control code to implement the above-described systems and methods, for example on a general purpose computer system or on a digital signal processor (DSP). The code is provided on a carrier such as a disk, CD- or DVD-ROM, programmed memory such as non-volatile memory (e.g. Flash) or read-only memory (Firmware). Code (and/or data) to implement embodiments of the invention may comprise source, object or executable code in a conventional programming language (interpreted or compiled) such as C, or assembly code. As the skilled person will appreciate such code and/or data may be distributed between a plurality of coupled components in communication with one another.

In a related aspect the invention provides a method of predicting the response of a patient following surgery, the method comprising: using a multianalyte detector to detect levels of biomarkers characteristic of the degree of activation of a set of complement cascade pathways wherein said complement cascade pathways include the lytic pathway and at least one of the lectin pathway, classical pathway and the alternative pathway; analysing said levels of biomarkers using model data defining a model having at least levels of said biomarkers as parameters to predict an outcome of said surgery from a set of outcomes comprising at least recovery and infection of said patient, and outputting data identifying said predicted outcome.

Preferably the levels of biomarkers are detected at a discrete set of times to provide time series data for the analysis, as previously described. In embodiments relative levels of the biomarkers are employed, in particular to compensate for a background or pre-existing activation of the complement cascade. In some preferred embodiments the different activations or fluxes in the complement cascade pathways are employed to identify a type of infection and to differentiate this from a predicted recovery process. In embodiments the system is configured, in particular, to identify/predict the onset of sepsis of the patient.

BRIEF DESCRIPTION OF THE DRAWINGS

These and other aspects of the invention will now be further described, by way of example only, with reference to the accompanying figures in which.

DETAILED DESCRIPTION OF PREFERRED EMBODIMENTS

We first describe a Procedure Outcome Predictor using the Complement Cascade (POPCC).

Figure 1:
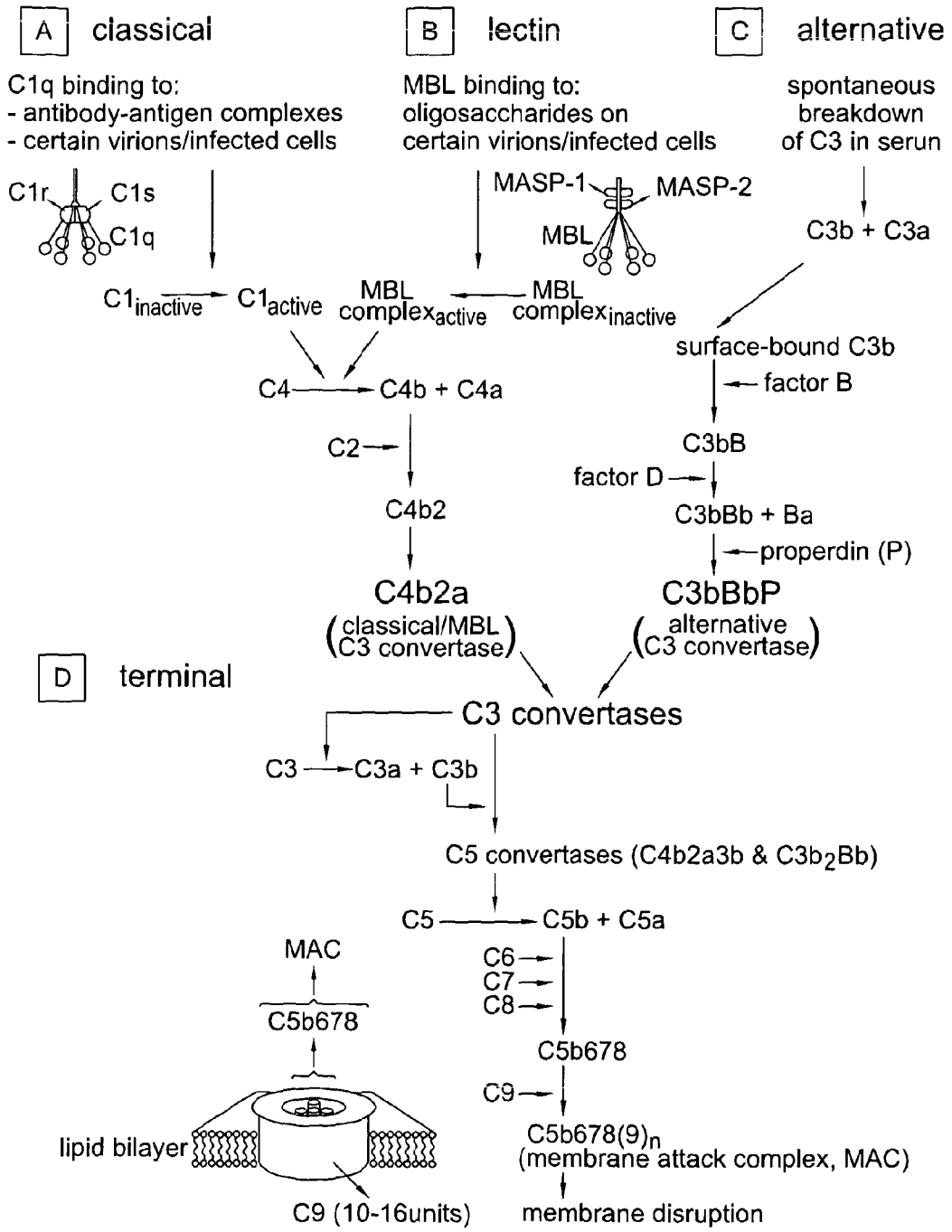
FIG. 1 shows the Complement Cascade, showing the Classical, Lectin and Alternative activation pathways leading to the Lytic pathway.
Figure 2A:
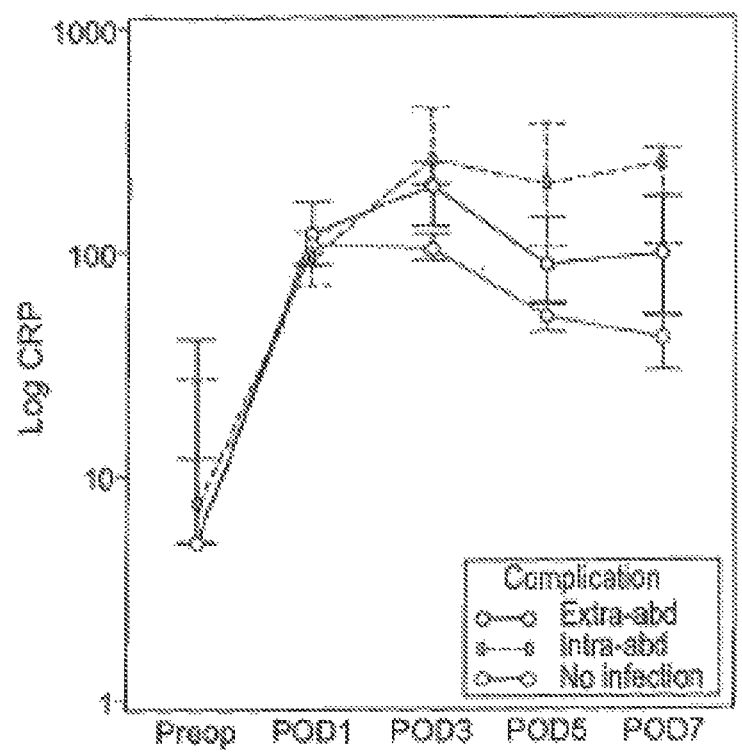
FIGS. 2a and 2b show, respectively, C-Reactive Protein (CRP) time course for post-operative days (PODs) for healthy recovery, intra-abdominal and extra-abdominal complication; and post-operatively for colorectal resection (colorectal cancer—CRC; and inflammatory bowel disease)
Figure 2B:
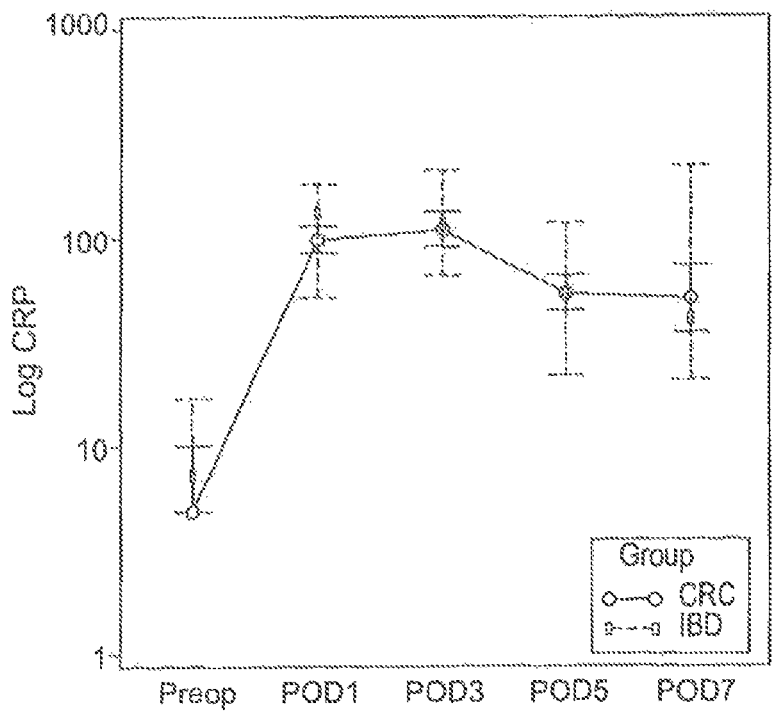

Referring to FIG. 2a, this shows CRP time course for post-operative days (PODs) for healthy recovery, intra-abdominal and extra-abdominal complication. FIG. 2b shows that a CRP-based POP for discharge even at day 5 would appear to be an absolute level and a falling trend in CRP concentrations (note the error bars—as a patient this is re-assuring). However POPs need not be simple trends down associated with recovery but should preferably point towards trends of reduced inflammation and infection. Preferably some or all correlation POPs above should to return to a norm or quiescent state.

More particularly, we have shown that a model of the Complement Cascade (CC) provides a better predictor of elective procedure outcome than C-reactive protein (CRP) and White Blood Cell (WBC) level monitoring.

Complement Cascade

The CC comprises of order 30 components which are present either as complete proteins or sub-units of these proteins with a collection of regulatory factors divided into three pathways.

The CC forms part of the innate response to infection providing two defence processes: opsonisation and the membrane attack complex. Early detection proteins trigger the remainder of the cascade providing primitive of antigen recognition of the surface of pathogens with some discrimination. Additional factors moderate the CC response providing a multiplexed response to an infection with postulated characteristic responses of the CC.

First Differential Hypothesis requires that the CC response is differential towards Gram+, Gram−, viral and fungal pathogens.

Pre-symptomatic Hypothesis requires the CC response to be detectable before the presentation of clinical symptoms.

Methodology for realising the two hypotheses is a multi-analyte absolute concentration determination of serum CC proteins with measured over a time course calibrates a CC model for determining relative pathway fluxes, component consumption, degree of regulation and CC dysfunction. CC model analysis against measured absolute concentrations leads to differential diagnoses.

Our Array Reader platform provides sufficient sensitivity, accuracy in a selectivity multi-analyte format for a rapid simultaneous detection of analytes. Characteristics of an appropriate technology are:
1) Rapid, simultaneous detection to prevent degradation of components in the serum
2) Absolute concentrations determinations
3) Accuracy of 10% or better based on the concentrations of the target proteins and how they change during activation.
4) Ideally;
   a. Small volume perhaps 200 μL
   b. Whole blood to minimise degradation in the processing
5) Near patient to provide minute-by-minute CC profiling.

Activators of CC

Lectin Pathway

Microbial surfaces notably microbial polysaccharides and some IgA

Classical Pathway

Antibodies of all types binding to the surface of pathogens usually microbial trigger the Classical Pathway including CRP which may be considered as a primitive antibody with a spectrum of specificities which are not particularly avid.

Alternative Pathway

Spontaneous attachment to all foreign surfaces, including surgical catheters, cell debris such as lipo-polysaccheride, some virus particles, Lytic Pathway Fibrinogen and the clotting cascade stimulate directly at C5a and concomitant stimulation from Alternate, Classical and Lectin pathways. The Lysis pathway leads to the formation of the membrane-bound, membrane attack complex responsible for the lysis of foreign organisms.

Markers of Activation

Flux through each of the activation pathways $J_A$, $J_C$, $J_L$ and the lysis pathway, $J_{Ly}$ are measured by the changes of the components of the pathway with respect to one another: The flux at species A is given by:

$$\frac{\Delta J}{J} = \frac{\Delta [A]}{[A]} \frac{v_f}{v_f - v_r}$$

where the forwards and backward rates are $v_f$ and $v_r$ respectively. Changes in the pathway concentrations over time define the flux parameters. Flux control points, and positive and negative feedback loops can then be seen. $J_A$ shows positive feedback with C3a.

First Differential Diagnosis—Time Evolution

G+ infection $J_A+J_L>J_C$, elevated $J_{Ly}$
G− infection $J_A>J_L+J_C$, elevated $J_{Ly}$
Viral $J_A>J_C+J_L$, depressed $J_{Ly}$
Fungal $J_A+J_L>J_C$, depressed $J_{Ly}$
Antibody response $J_V>J_A+J_L$ elevated $J_{Ly}$ Serum Concentration Markers—Time Evolution $J_C$ activation—increasing C4a, depletion C1,C1$_q$, increasing CRP $J_L$ activation—increasing C2b, depletion factor H, Factor I $J_A$ activation—increasing C3a, decreasing C3, decreasing fH, fI, fD, decreasing properidin initially then rising.
$J_{Ly}$—increasing C5a, decreasing C6-C9

Absolute Concentrations—Time Evolution

Concentrations at t<0 are generally within normal ranges 1-10 µg ml$^{-1}$ which can increase to 2 mg ml$^{-1}$ over time. Initially there is a drop in the levels of some C proteins notably C1, MBL C3 as the serum concentrations are used up covering surfaces.

Correlated Diagnostics

Correlated or anti-correlated trends in more than one species within pathways are characteristics of system-level responses:
- depletion of proteins correlates with reduction in regulatory proteins
- sepsis corresponds to a lack of regulation of the immune response leading to a system runaway.
- correlations across the cascade indicate patient-system-level control.

Acute Phase Proteins (ACP)

In addition to the CC, the acute phase proteins are also regulated during infection and detection of these may be incorporated into the microarray and/or analysis.

C-Reactive Protein (CRP)

We now describe some background on CRP, helpful for understanding embodiments of the invention. CRP has two fH binding sites to that high CRP removes fH which down regulates the Alternative and Lectin pathways.

CRP binds to phosphocholine at its $Ca^{2+}$ binding site and to phosphoethanolamine, microbial surface proteins, chromatin, histones, fibronectin, small nuclear ribonucleoproteins, laminin, and polycations. These CRP-ligand interactions recognize damaged or apoptotic cells and bacterialpathogens. CRP activates complement by the classical pathway. Even though CRP is also reported to bind inhibitory complement regulators such as FH, the basis of such an interaction is less clear and appears to contradict CRP activation of complement by the classical pathway. Interestingly, individuals who are homozygous for the AMD risk His-402 FH allotype show a 2.5-fold higher level of CRP in the retinal pigmental epithelium.

CRP is not thought to be a good predictor of outcome following cardiac surgery within 48 hours.

Production in the liver occurs 6 hours after inflammation and decays 50 hours after inflammation.

Intraabdominal infections are caused mainly by anastomotic leaks and represent a serious complication. Diagnosis is usually made when patients become critically ill. Though inflammatory markers, including C-reactive protein (CRP) and white blood count (WBC), may contribute to an early diagnosis, their clinical roles remain unclear. The diagnostic accuracy of continuous tests depends on the choice of cut-off values. We analyzed the diagnostic accuracy of serial CRP and WBC measurements to detect infectious complications after colorectal resections.

However, CRP levels change considerably during the postoperative course in both uncomplicated and complicated cases, and they are not specific to any one kind of complication.

The biological marker CRP reflects inflammation and therefore the risk of poor outcomes, and there is increased risk of poor outcomes among patients with preoperative elevations in CRP. Nonetheless, the significance of postoperative CRP after potentially curative nephrectomy for localized RCC remains unknown.

Sensor System

An example of a preferred biosensor array for plasmon resonance-based sensing of a plurality of different biological targets simultaneously comprises a transparent substrate having a surface bearing a plurality of assay spots for plasmon resonance sensing, each of said assay spots comprising a discrete metallic island, a said metallic island comprising a plurality of metallic nanoparticles to which are attached functionalising molecules for binding to a said biological target, different said islands bearing different said functionalising molecules for binding to different ones of said biological targets, and wherein total internal reflection of light at said surface at a wavelength at or near a said plasmon resonance results in scattering of said light away from said surface, said scattering being modulated by said binding of said biological targets.

In some preferred embodiments the metallic nanoparticles, which are preferably of gold, have at least one dimension of less than 30 nm, preferably less than about 25 nm. At this point the interaction between the evanescent wave and the metal changes from being dominated by absorption to being dominated by scattering. In some preferred embodiments the nanoparticles form optical antennas, that is, in embodiments, pairs of rod-like nanoparticles separated by a gap of similar dimensions to the width of a rod. More generally such an optical antenna may comprise an adjacent pair of nanoparticles, preferably each with a length:width aspect ratio of greater than 2:1, and preferably having adjacent ends separated by a gap of less than 100 nm, preferably less than 50 nm. In some preferred embodiments these comprise rod-shaped nanoparticles but other shaped nanoparticles may also be employed, for example generally triangular nanoparticles, or a combination of different shaped nanoparticles such as a rod-shaped and an adjacent generally triangular nanoparticle.

In particular, preferably each nanoparticle of an adjacent pair of nanoparticles has a length which is resonant for a plasmon wavelength in the metal, more particularly having a length which is approximately equal to an odd integral number of a plasmon half-wavelengths. The plasmon wavelength can be determined from the complex refractive index of the metal (for example 0.188+5.39i for the complex refractive index of gold) and from the wavelength of the illuminating light; preferably each nanoparticle of the pair of nanoparticles has a plasmon resonant length corresponding to an illuminating light wavelength of between 150 nm 1500 nm, more preferably 250 nm to 1000 nm, most preferably 450 nm to 900 nm (for 1 and/or 3 plasmon half-wavelengths). Preferably each of the adjacent pair of nanoparticles have substantially the same resonant length.

Figure 3A:
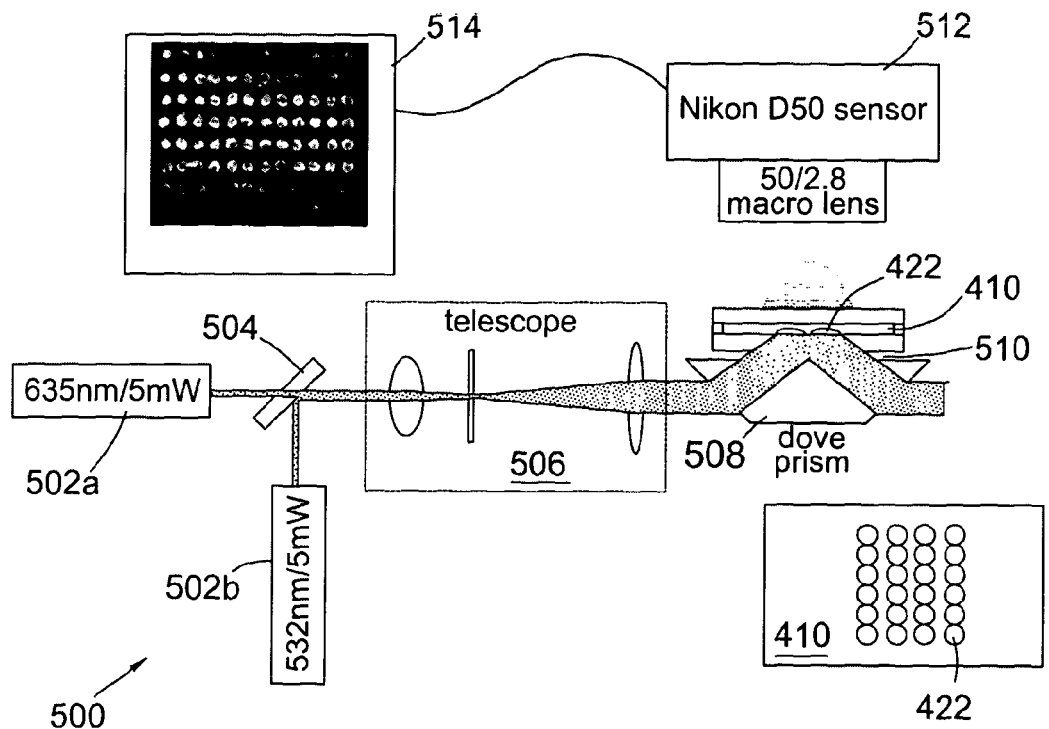
FIGS. 3a and 3b show example apparatus for complement cascade biomarker level detection using plasmon resonance.

FIG. 3a shows an example of scattered light reading apparatus 500 for reading assay spots using light scattered by plasmon resonance, modulated by the binding of one or more targets to one or more functionalising molecules of the array. The apparatus 500 comprises a pair of light sources 502*a*, *b*, in the illustrated example lasers although light emitting diodes may alternatively be employed. The wavelengths of these lasers are selected so as to straddle a plasmon resonance, as illustrated at 635 µm and 532 µm. The beams are combined by beam splitter 504 and provided through a telescope 506 to the microarray 410 which is placed on a totally internally reflecting surface of a Dove prism 508, coupled by index matching fluid 510. A colour digital camera 512 catches an image of the scattered light from the microarray which is provided to a computer system 514 for processing the image to identify and monitor binding kinetics of target molecules to the array. Colour camera 512 may be replaced by one, two or more monochrome cameras and, where two wavelengths are employed, wavelength selection may be performed by one or more dichroic mirrors. Preferably, but not necessarily, the imaging device has a substantially linear response to light intensity variations.

Figure 3B:
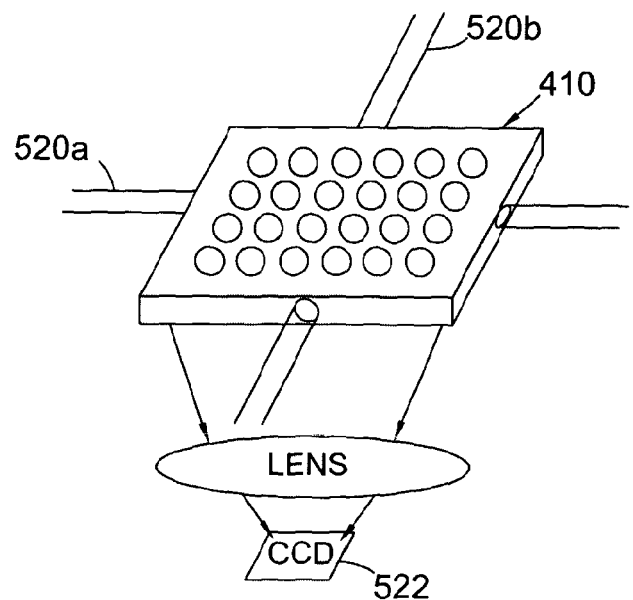
Figure 5A:
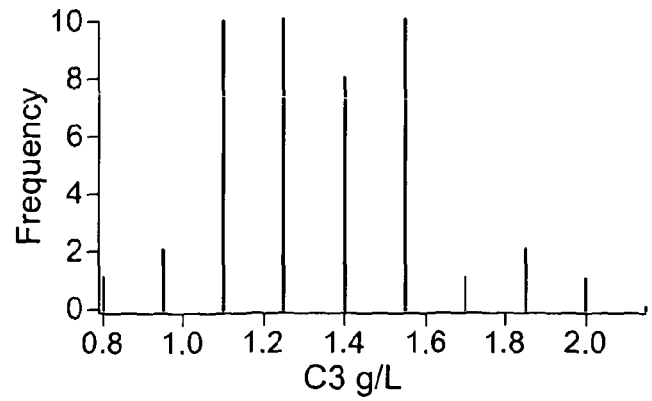
FIGS. 5a to 5d show distributions of initial marker concentrations for, respectively, C3, C4, IgG, and CRP.

FIG. 3b shows an alternative configuration in which incident light is provided by index matched fibres 520a, b into two edges of the array 410 and waveguided within the thickness of the array. In this illustrated embodiment darkfield scattered light from the array is imaged through the back surface of the array onto a CCD (charged coupled device) or CMOS sensor 522. Preferably, as shown in FIG. 5a, light of two different wavelengths is used to illuminate the array and the sensor is configured to selectively detect each of these wavelengths, for example by filtering or by time multiplexing the illumination. Preferably, for increased sensitivity, the illuminating light is modulated and phase sensitive detection of the scattered light is employed.

In some preferred implementations of a disposable biosensor array rather than index matched fibres being used to couple light into two edges of the array, one or more laser diodes is mounted on one or more sides (edges) of the array in order to facilitate simple interfacing to apparatus for interrogating the array (by means of straightforward electrical connections to the laser diodes).

A substance to be analysed, for example blood serum, may be provided to the microarray for sensing by, for example, a syringe coupled to a duct above the assay spots to flow the substance, for example serum, over the microarray. Embodiments of the apparatus permit samples of bloody fluid to be analysed directly (optionally diluted, for example with saline) because, in embodiments the use of some spots as controls enables compensation for non-specific binding. In more sophisticated embodiments a microfluidic fan-out along one or more edges of the array of spots may be provided.

Figure 4:
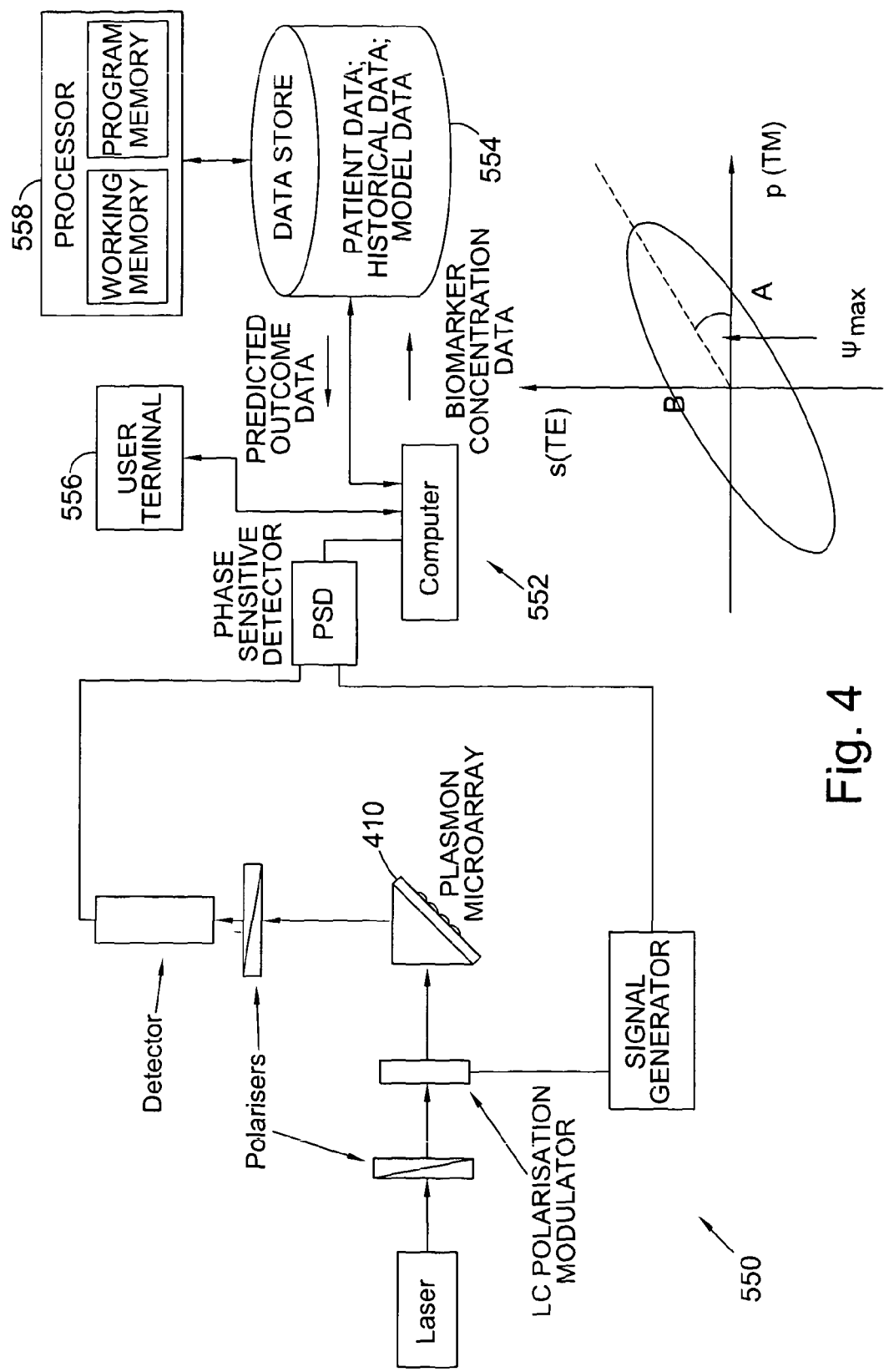
FIG. 4 shows analytical and data processing apparatus configured to implement embodiments of methods according to the invention.

Referring now to FIG. 4, this shows apparatus 550 which analyses the totally internally reflected light rather than the scattered light from the microarray.

Referring to the analytical system 550, If linearly polarised light with both TM and TE polarisations in incident upon the plasmon resonance system, then the TM polarised component undergoes this phase change, whereas the TE polarised component does not. The result of having two orthogonal components phase shifted with respect to each other is that the light reflected from the plasmon resonance system becomes elliptically polarised. Due to the fact that the phase changes rapidly as the plasmon resonance is traversed, it follows that the ellipticity and orientation of the polarisation ellipse also changes rapidly. Only the change in the azimuth of the polarisation ellipse may be considered since the variation in this is greater, as a function of the refractive index of the bounding dielectric medium, than is the ellipticity. It can be shown through multi-layer optical modelling that the azimuth of the ellipse is rotated by approximately 1° for a refractive index change of only $5 \times 10^{-5}$ RIU. Therefore, all that is needed to produce a sensitive refractive index sensor is an accurate and sensitive way to measure the rotation of the polarisation ellipse.

If a polariser were placed in the path of the reflected beam, before a detector and rotated through an angle $\phi$, then the signal obtained as a function of the angle of the polariser would show a cosine squared dependence. The angle at which the maximum in this dependence occurs corresponds to the azimuth of the polarisation ellipse. If the plane of polarisation of incident light upon the plasmon resonance system is dithered sinusoidally, and the signal at this dither frequency monitored, then the differential of the $\cos^2 \phi$ curve is obtained as a function of the polariser angle. The zeros of this differential signal correspond to the maxima and minima of the $\cos^2 \phi$ curve (the azimuth and the azimuth ±90°). Therefore, if the angular position of a zero is determined, the azimuth (or the azimuth ±90°) is found, and, if the refractive index of the bounding dielectric medium is altered, the angular position of the zero in the differential signal also changes.

Continuing to refer to FIG. 4, the analytical system 550 is coupled to a computer system 552 which performs signal processing on the data from the apparatus to determine biomarker level data representing levels of a plurality of biomarker levels of the complement cascade (CC). The system also interacts with a database 554 which includes a data to implement a model as described above to predict patient outcome, and provides a user terminal 556 for interacting with the system and outputting the prediction data. In embodiments the database is coupled to a further computer system 558 comprising working memory and program memory, the program memory storing code to use the model data to predict the outcome of a medical procedure on a patient as described.

In embodiments the data store 554 stores patient data, more particularly a time series of patient complement cascade data representing a one or more patient recovery pathways, a time series of cohort complement cascade data representing one or more cohort recovery pathways derived from a set of patients (labelled as historical data in FIG. 4), and model data representing a statistical model for determining one or more deviations of the patient recovery pathway(s) from the cohort recovery pathway(s).

A pathway may be defined by some mathematical combination of the levels of biomarkers, for example a sum of two divided by the level of a third, or the like. In embodiments the model is a Bayesian model in which, broadly speaking, a prior represents an expected patient recovery pathway (for example, derived by Bayesian analysis of the collected data) and a calculated deviation represents a deviation of the patient recovery pathway from this, for example:

$$P(\text{outcome\_path}|\text{observed\_path}) = P(\text{observed\_path}|\text{outcome\_path}) \cdot P(\text{outcome\_path})$$

The techniques we describe, more particularly the further computer system 558, may be implemented separately to the analytical system described above. We will now describe further details of prediction techniques using measured levels of complement cascade biomarkers derived from other microarray technology (in one embodiment, a multi-array plate from Meso Scale Discovery, LLC, MD USA—'MSD').

Complement Path Outcome Prediction

We have performed serial measurements of the concentration of CC components during the peri-operative period to develop a quantitative, mechanistic/mathematical model for the response and its relationship to patient recovery. The measured CC response is capable of informing about the expected rate of recovery, the likelihood of complications, and the nature of such complications. This can offer a pre-symptomatic guide to differential diagnosis with patterns of activation characteristic of Gram positive, Gram negative, viral and fungal infections. The measured CC "impulse" response is capable of the stratification of patients and may further be employed to selectively perform pre-operative priming and activation of the CC.

For an example trial major pelvic surgery was chosen as it provides a statistical secondary infection rate of 23% with 12% developing sepsis. Without employing the CC response approximately 60% of secondary infections are identified, with a 55%:45% Gram+:Gram− ratio. The CC temporal profile shows the initial surgical insult and a subsequent differential response to secondary infection during recovery. Importantly, C proteins are constitutive blood proteins and activation can be triggered by surgical insult within minutes: this may be compared with CRP and white blood cell (WBC) count markers of recovery (for example a patients may be discharged against CRP levels below 150 mg $L^{-1}$ and falling) where leukocytosis and CRP responses peaks 48 hours post surgery (laparoscopic or conventional). Presymptomatic prediction of the progress of recovery is important as it impinges directly on clinical decisions. Blood can be recovered from swabs during the operation and the C activation status of the recovered blood or transfused blood and its subsequent impact on systemic C activation is determined. Further, the ability to stratify patients according to the predicted recovery and likelihood of complications allows healthcare providers to plan the provision and utilisation of varying levels of in-patient care, and in-hospital mortality rates may be reduced by reducing the 'time to rescue' (the speed of recognition and management of complications).

An accurate, pre-symptomatic differential diagnosis can be generated, based on the differential activation of flux through the activation and terminal pathways of the CC, and thus the 'time to rescue' may be greatly reduced. The different pathways are differentially stimulated by different immune challenges and are highly regulated by a series of blood and cell-associated factors.

Differential activation within a pathway may be identified based on relative consumption of factor B in the alternative pathway, C4 and C2 in classical and lectin pathways, and C5-C9 in the terminal pathway. The CC can also be triggered by activation of the haemostatic system, notably by thrombin cleavage of C5.

A trial was performed to build a mechanistic kinetic model of the Complement Cascade in response to a surgical insult to monitor patient recovery and predict outcome, as follows:

1) Collect blood samples from patients undergoing elective colorectal surgery and perform plasma protein concentration analysis of the patient's blood on a peri-operative time course and during recovery (from admission to discharge).
2) Perform EDTA-plasma assays on 4 C activation markers and CRP: CRP, C2a, C3d, C4d, Bb and TCC (using an MSD multiplexed assay platform).
3) Derive a temporal profile for the response to the surgical insult and recovery (and compare with CRP and WBS analysis).
4) Construct a model for the CC to determine differential activation and flux in the pathways of the CC and correlate with clinical recovery.

Complement (C) proteins form a cascade in the blood which responds to the surgical insult and the presence of foreign pathogens. C removes infection in two ways: 1) pathogen opsonisation followed by destruction by macrophages; and 2) formation of the membrane attack complex which causes lysis in bacteria. Opsonisation is the more important by possibly a factor of 100. C activation in the blood is observed within minutes of the initial surgical insult and the concentration of C activation makers C3dg, C4d, Bb and terminal cascade complex (TCC) is followed over a time course peri-operatively. The initial response or "impulse response" points towards a C capacity within the patient and indicates susceptibility to secondary infection or time to recovery. The plasma concentrations of the C-activation biomarkers are also correlated with patient performance when patients are subjected to enhanced recovery interventions—such as physical stress reduction (with the use of minimally invasive/laparoscopic surgical techniques), patient temperature regulation during the operation, and regional anaesthesia. Differential C activation of the classical, alternative, lectin and terminal pathways shows discrimination between Gram positive, Gram negative, viral and fungal secondary infections, and allows early identification of secondary infection pre-symptomatically from the differential marker temporal profiles.

The assay schedule is detailed in Table 1 below. The four trial samples mentioned are taken at time intervals that capture the impulse response of the patient's CC (t=0, +1 hr, +4 hrs, +8 hrs, +12 hrs; also t=−24 hrs for normalisation).

TABLE 1

Time Course Sampling for CPO trial

| Time Point | Time of Test | Routine Test | Additional Trial Test | Trial Assays | Day Timings |
|---|---|---|---|---|---|
| 1 | t = −1 Pre-admission clinic CONSENT | ROUTINE | | C4, C5, IgG C3dg, C4d, Bb, TCC, CRP | t = −1 day |
| 2 | Pre-operatively t = 0 Under anaesthesia | | Trial Sample NO. 1 | C4, C5, IgG C3dg, C4d, Bb, TCC, CRP | t = 0 9:30 hrs |
| 3 | t = 1 hr Under anaesthesia | Knife-to-skin plus 30 mins | Trial Sample NO. 2 | C4, C5, IgG C3dg, C4d, Bb, TCC, CRP | 10.30 hrs |
| 4 | t = 2-4 hrs immediately post surgery | ROUTINE | | C4, C5, IgG C3dg, C4d, Bb, TCC, CRP | 1330 hrs (equivalent to t + 4 hrs) |
| 5 | t = 8 hrs | | Trial Sample NO. 3 | C4, C5, IgG C3dg, C4d, Bb, TCC, CRP | 17:30 hrs |
| 6 | t = 12 hrs | | Trial sample NO. 4 | C4, C5, IgG C3dg, C4d, Bb, TCC, CRP | 21:30 hrs |
| 7 | t = 24 hrs | ROUTINE | | C4, C5, IgG C3dg, C4d, Bb, TCC, CRP | 09:30 hrs |
| 8 | t = 36 hrs | ROUTINE | | C4, C5, IgG C3dg, C4d, Bb, TCC, CRP | 21:30 hrs |
| 9 | t = 48 hrs Some Patients Discharged Complications Develop | ROUTINE | | C4, C5, IgG C3dg, C4d, Bb, TCC, CRP | |
| | t = x1 | Routine Tests as these occur | | C4, C5, IgG C3dg, C4d, Bb, TCC, CRP | |
| | t = x2 | Routine tests as these occur | | C4, C5, IgG C3dg, C4d, Bb, TCC, CRP | |
| 10 | Discharge | | | | |

The assays deployed for the biomarkers of C activation are: C3dg, C4d, Bb, TCC (terminal complement complex) and the acute phase marker, CRP. For the target biomarkers antibodies to neo-antigens that are revealed post enzymatic cleavage or complex formation are used as capture antibodies on the surface of the MSD platform. The C proteins are then detected with polyclonal antibodies labelled with a ruthenium tagged antibody. Whole EDTA-stabilised plasma is then incubated in the 96-well format of the platform; all 5 assays, including calibration curves, are run simultaneously. Electroluminescence from the ruthenium complex is collected and quantified automatically. Absolute measurements of C proteins are performed using standardised fully activated serum (available via Prof B. Morgan, Department of Medical Biochemistry and Immunology, Cardiff University, UK, from the 'Complement Standardization Group') which contains a constant amount of activation products from all complement pathways. C activation relative to this standard can then be determined. This leads to an array of C activation markers that is tested against the patient cohort. This array may also include some of the other pathway markers, and may potentially be used for a routine clinical test.

Various outcome predictors and biomarker patterns of differential diagnosis may be derived empirically from statistical analysis of the concentration-time-clinical outcome correlations and mechanistic outcomes including the C impulse response, activation pathway markers and fluxes correlated with known diagnostics such as identification of secondary infection pathogens. In particular there are strong correlations between the initial impulse response (the degree of C activation compared to fully activated samples) and recovery. An initial assessment of C capacity from the levels of activation is thus useful as a predictor of outcome and/or susceptibility to secondary infections. A kinetic model may be employed to capture the "impulse response" (the initial <24 hrs or <18 hrs response) and to assess the C capacity based on a patient's C levels and rates of production. The impulse response may also be used to classify patients into quartiles with respect to the fully C-activated serum levels, which also correlates with outcome and effective C response to secondary infection. The C response to secondary infections is faster than the presentation of symptoms, leading to pre-symptomatic first differential diagnosis into gram+, gram−, viral or fungal.

Descriptive analysis of the captured analytical data may include mean and/or standard deviation values optionally together with confidence intervals. If the data are not normally distributed and cannot be transformed then they may be summarised using medians and inter-quartile ranges. Plots are made of all variables over time and separate plots are made of groups of patients experiencing different outcomes. The data is examined for multiple co-linearity and the most significant variables. Two of the main outcomes of colorectal surgery are either normal progress with discharge home within 72 hrs or sepsis resulting from different groups of microorganisms (G+ bacteria, G− bacteria, fungi and viruses), either individually or in combination. Comparisons are made between subgroups, such as those recovering normally and those developing sepsis. Multiple regression analysis may be employed to select complement cascade species for a model of the development of complications compared with normal recovery. Variables are preferably measured using microarray methods such as those described above, but alternatively conventional hospital laboratory methods may be employed (or both, compared, selected or combined for example using Bland Altman analysis, which can be used to determine the limits of agreement between them, together with confidence intervals). In embodiments markers used include at least CRP, C3, C4 and IgG. In embodiments data was analysed using SPSS v15 and Stata® (from StataCorp LP, Texas, USA).

The CPOP trial recruited patients between November 2010 and February 2011; the population demographics for the trial are summarised in Table 2 below.

TABLE 2

CPOP Trial Demographics

| Property | | | |
|---|---|---|---|
| Number of Patients | 45 | Patients Approached 52 | Recruitment Rate 85% |
| Age of Participants | Mean 64 yrs | Lower Quartile = 53 | Upper Quartile = 72 |
| Length of Stay | Mean 200 hrs | Lower Quartile = 94 | Upper Quartile = 199 hrs |
| Surgery Duration | Mean 154 hrs | Lower Quartile = 105 | Upper Quartile = 205 |
| Males | 25 | | |
| Females | 20 | | |

Determining the initial spread in the distribution of markers pre-operatively is a useful first step in the stratification of patient's response and predictors of outcomes. The initial values can be used to set the normalised level for each patient at the beginning of the patient pathway, as shown in Table 3.

TABLE 3

Initial Marker Concentrations

| Marker | Mean value | Lower Quartile | Upper Quartile |
|---|---|---|---|
| C3 g/L | 1.4 | | |
| C4 g/L | 0.27 | | |
| CRP | | | |
| IgG | 9 | | |

Figure 5B:
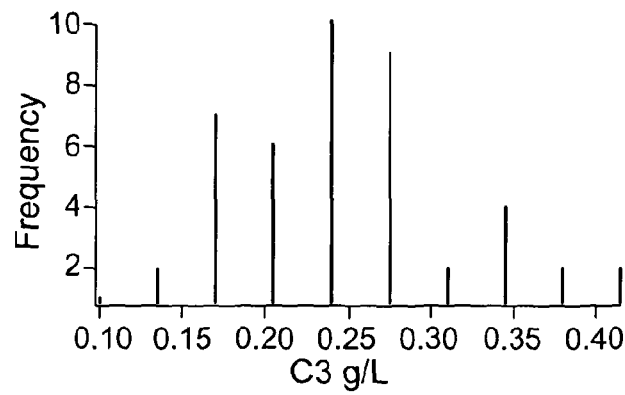
Figure 5C:
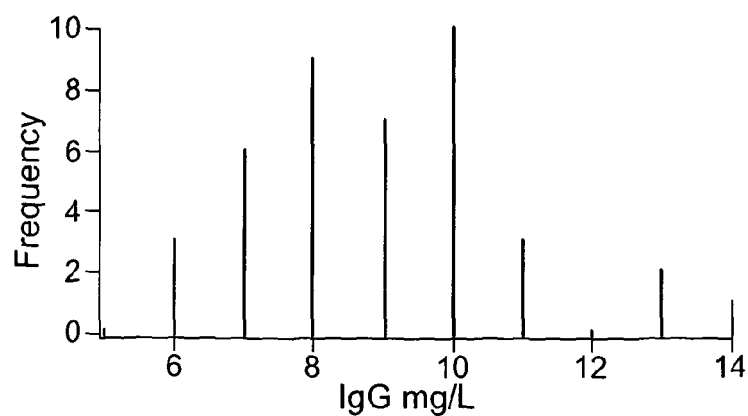
Figure 5D:
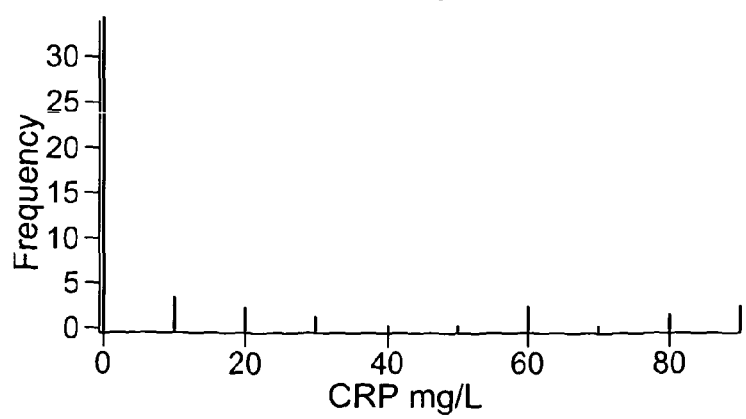

The initial C3 concentration may be divided into 10 bins each of 0.5 SD width to give the histogram shown in FIG. 5a with a minimum value C3 Min=0.94 g/L reported for patient CPOP030 and the maximum value C3 Max=CPOPO40 2.07 g/L. As similar distribution analysis can be performed for C4, IgG and CRP as shown in FIGS. 5b to 5d. The minimum and maximum values are summarised in Table 4, with notable high values and the patient identifiers.

TABLE 4

Initial Marker Concentrations

| Marker and Normal Range | Min Value | Max Value |
|---|---|---|
| C3 g/L (0.68-1.80) | 0.94, CPOP030 | 2.07, CPOP040 |
| C4 g/L (0.18-0.60) | 0.12, CPOP030 | 0.43, CPOP012 |
| IgG g/L (5.8-15.4) | 3.5, CPOP048 | 16, CPOP012 |
| CRP mg/L (0.05-400) | <3 (Normal) | 97 CPOP012 Notable Highs include CPOP12 = 97 CPOP49 = 95 CPOP24 = 81 CPOP26 = 63 CPOP42 = 61 |

Figure 6:
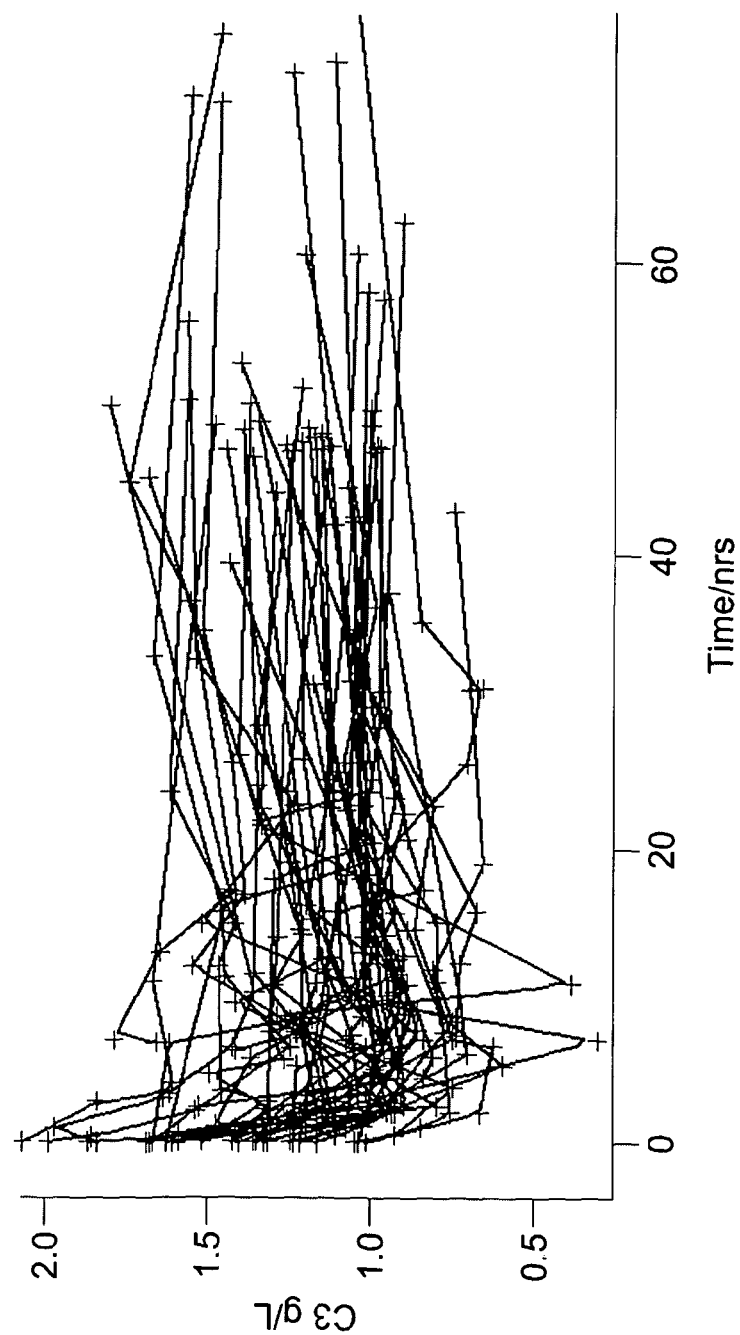
FIG. 6 shows un-normalised C3 patient nomograms for a cohort of patients.

The recovery of a patient may be represented in a nomogram as a time series in a number of CC parameters, and this may be used for outcome prediction. FIG. 6 shows unnormalised C3 patient pathways, showing a spread of values (also the data of FIG. 6 were collected at slightly different time points, which means the time points for each patient are slightly different). There is evolution of the recovery parameters in time but because of the spread in the initial values of the parameters there is no obvious pattern.

Therefore we perform normalisation of the patients numbers against their starting values (as marker of health on admission, albeit all patients are entering hospital with some sickness). The production of C3 and C4 are part of the acute phase response protein synthesis by the liver is rapid so that even with a systemic infection the levels of C3 and C4 may not appear outside the normal range. Consequently it can be difficult to take single-point measures of complement say during a visit to a clinic and diagnose complement consumption. On admission therefore unless patients have specific depletion problems such as C2 or C4 depletion associated with pathologies, the initial levels of C3 and C4 are those that are controlled by the positive and negative feedback control of the C cascade. The initial (C30) and initial (C40) values are therefore reasonable measures of the performance of the C cascade.

Figure 7A:
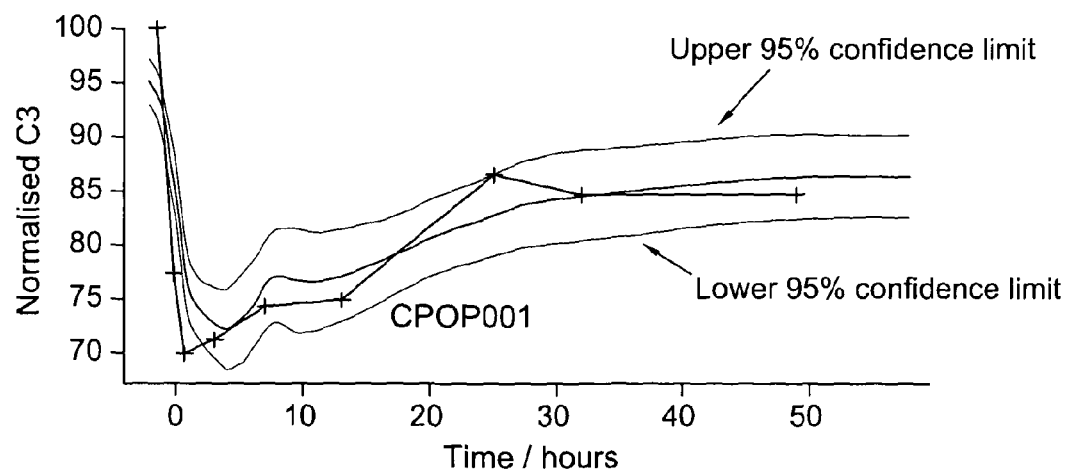
FIGS. 7a and 7b show, respectively, a normalised C3 impulse response for a cohort of patients showing the average curve and 95% confidence limits (which may be employed as a cohort recovery pathway nomogram) and an example of a patient recovery pathway; and normalised cohort recovery pathways (nomograms) for C3, C4 and IgG, also showing 95% confidence limits.
Figure 7B:
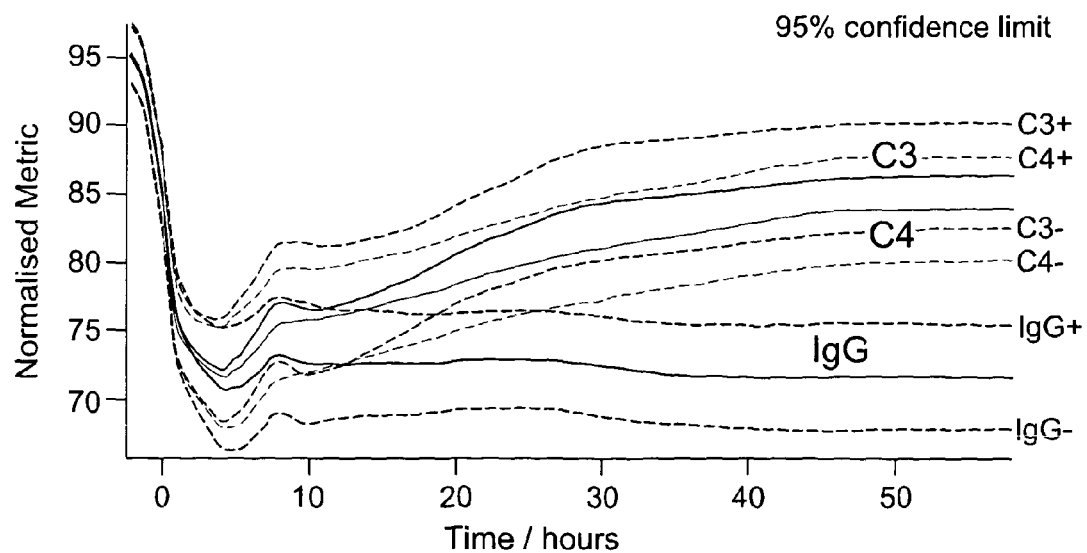

Normalisation to the C30 values and performing a linear interpolation between the points on a data set allows all of the patient data to be averaged together to produce a mean-value average of 45 patients. The nomogram and 95% confidence limits (1.96*SD/√n) can be calculated and are shown in FIG. 7a, together with the patient pathway for patient CPOP001. There was no selection of patients into the average curve and the deviations from patient complications present in the time course from 5-15 hrs contribute only 1/45 to the total shape of the nonogram. FIG. 7b shows a set of CC curves, for normalised levels of C3, C4 and IgG, together with +/−95% confidence limit curves (as dashed lines).

Nomograms of medical observations such as temperature, blood pressure, blood cell counts and the like may also be employed, for comparisons of recovery end-points with the CPOP markers.

Pathway Scores and Identification of Complications

Figure 8A:
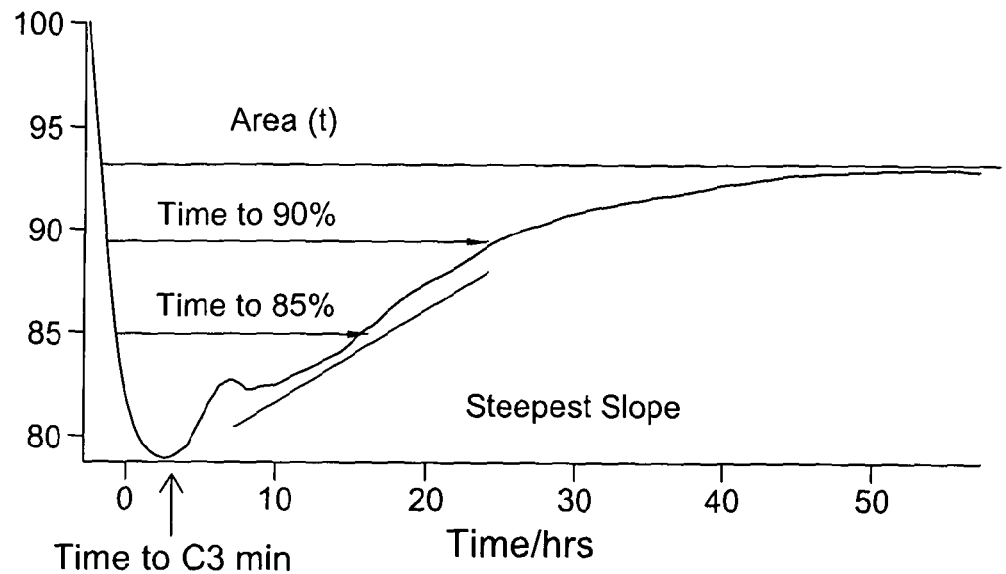
FIGS. 8a and 8b show, respectively, example patient-cohort recovery pathway deviation metrics which may be employed as recovery parameters including: time to marker minimum, time to a threshold percentage recovery, steepest recovery slope, and area bounded by the curve; and a graph illustrating that minimum values of C3 and C4 are well-correlated with pathway scores.

Any properties of the CC nomograms that evolve in time may be used to monitor the recovery or predict the outcome of the patent's procedure. The nomogram for nC3 (normalised C3) is shown in FIG. 8a and indicates a number of possible recovery parameters may be tested against, for example, the recovery end-point. The discharge time is a reasonable proxy for the recovery end-point and/or a Clavien Score may be employed [Clavien, P. A., et al. "The Clavien-Dindo Classification of Surgical Complications: Five-Year Experience", Annals of Surgery 2009, 250(2), 187-196]: Both can be used as external measures of recovery. From the analysis of the nomograms however, internal measures of recovery are also possible, such as time to a threshold percentage of a CC marker recovery, for example 80% cC3 recovery. The internal and external end-points lead to a matrix of correlations of procedure outcome predictors (see also Table 6 later).

Figure 8B:
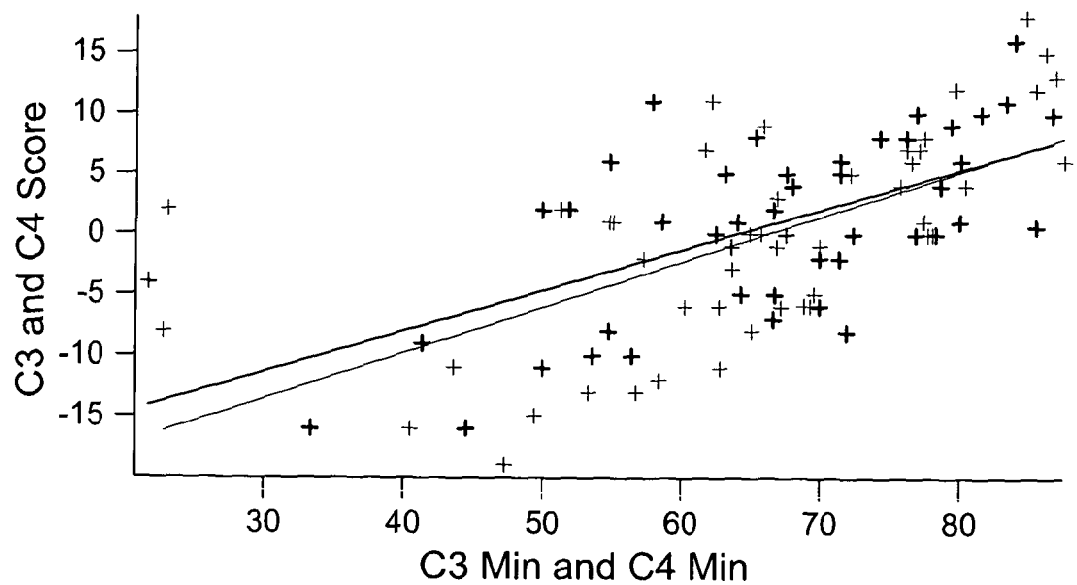

Although pathways scores are useful tools, a pathway score need not be calculated directly. FIG. 8b shows a graph illustrating that minimum values of C3 and C4 are well-correlated with pathway scores, so that, in principle, a minimum value of C3 or C4 determined from a pathway may be used as a proxy for the respective pathway score. More particularly, FIG. 8b shows a correlation between C3_score and C3_min (r=0.63) and C4_score and C4_min (r=0.62), illustrating that C3_min and C4_min are good predictors of C_pathscores (n=45). Thus in principle pathway measures such as those shown in FIG. 8a may be employed as a proxy for a pathway score—and thus in embodiments an effective pathway score may be determined by determining one or more of: a minimum value of a complement cascade marker, a time to a minimum value of a complement cascade marker, a steepest recovery slope of a complement cascade marker, and an area bounded by a complement cascade marker recovery pathway.

Figure 9:
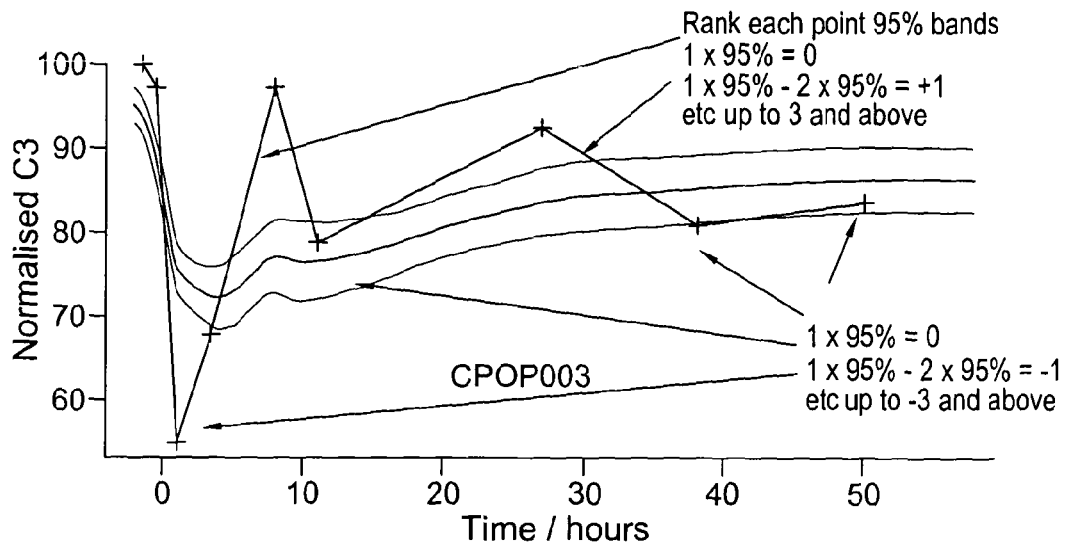
FIG. 9 illustrates calculation of a patient recovery pathway score for an example patient.

One example of a pathway score (the skilled person will recognise that many others may be derived) counts the number of times a patient recovery falls below the 95% confidence limits of the nomogram for more than one biomarker. FIG. 9 shows an example cumulative pathway score based on the 95% confidence deviations:

Within the 95% confidence limit score 0
Within the 1-2 95% confidence limit scores +1 or −1
Within the 2-3 95% confidence limit scores +2 or −2
Above the 3 95% confidence limit scores +3 or −3

Figure 10A:
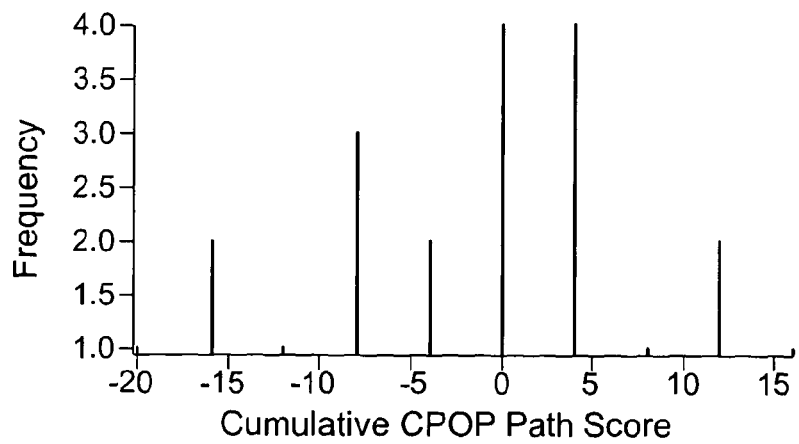
FIGS. 10a and 10b show example pathway score distributions for a set of trial patients for, respectively, C3 (FIG. 10a) and C4 (FIG. 10b)
Figure 10B:
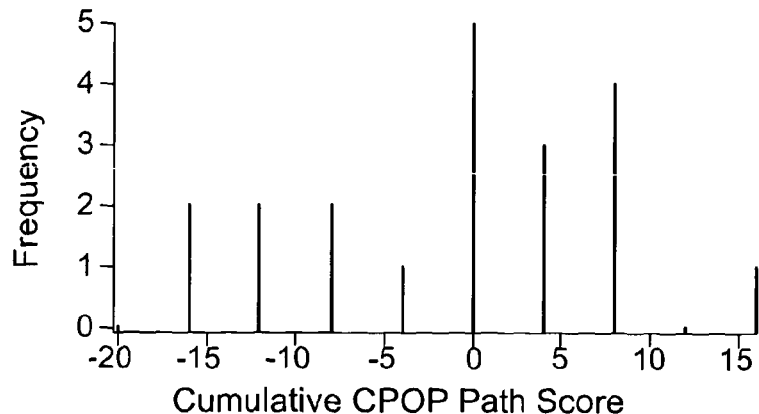
Figure 11A:
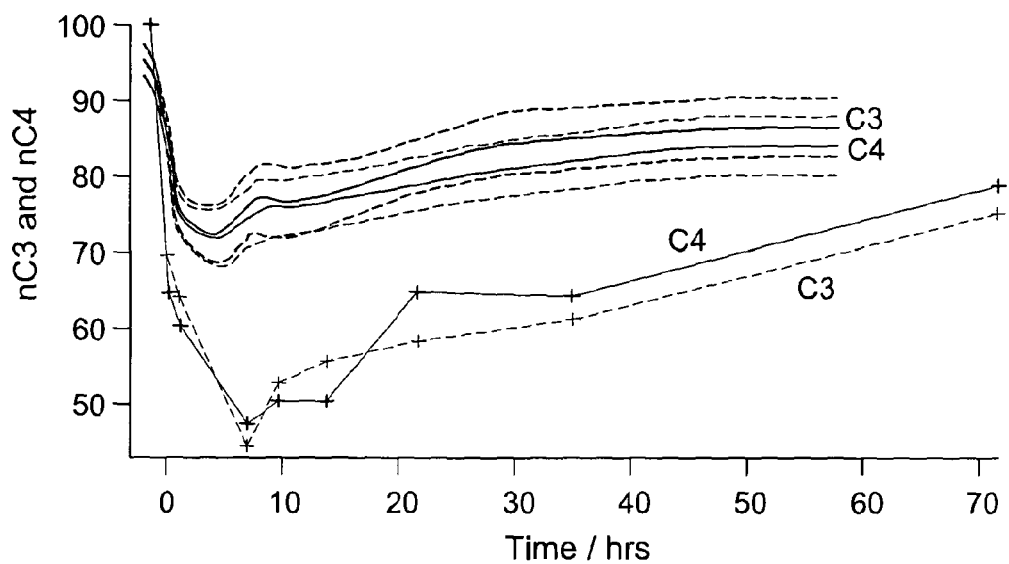
FIGS. 11a and 11b illustrate C3 and C4 patient recovery pathways for two example patients (CPOP025 and CPOP028 in the example table in the description) illustrating complications.
Figure 11B:
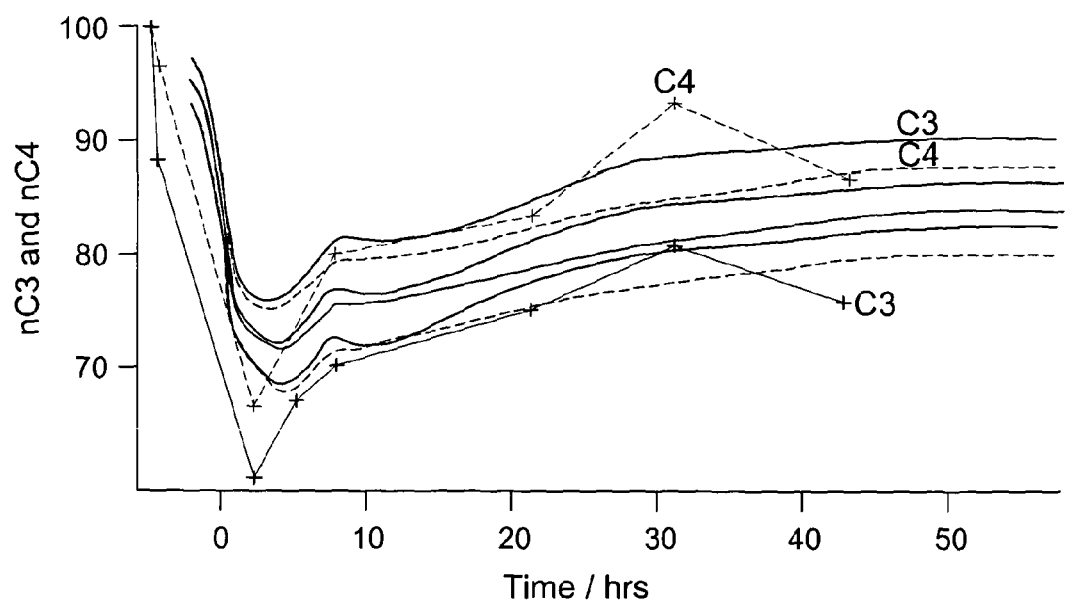

Based on this scoring, the evolution of the patient's recovery can be calculated in time and the early stage scores can be used to predict problems or classify patients into strata as likely (or not) to show complications. Calculating the 50-hr pathway scores for all 45 patients in the trial leads to the distributions for nC3 and nC4 shown in FIG. 10. The majority of patients have a pathway score of between 0 and 5 although a number show a score greater than 10. However, mechanistic requirements—that is a consideration of the model of the underlying complement cascade—indicates that negative pathway scores point towards complications. The selection of patients based only on their pathway scores provides a first identification of recovery complications. The complications rate predicted by the Pathway Scores are summarised in Table 5 below, with two example complications shown in FIG. 11 (CPOP025 and CPOP028 in FIGS. 11a and 11b respectively). Some patients are C3 complications only giving a C3 complication rate of 31%: C4 predicts 20% complication rate and there are differential activations between some of the patients showing complications.

TABLE 5

Complications Identified by the CPOP pathway Scores for C3 and C4

| Patient Number | C3 Score | C4 Score |
|---|---|---|
| CPOP010 | −12 | −10 |
| CPOP012 | −16 | −16 |
| CPOP015 | −6 | −6 |
| CPOP018 | −11 | −9 |
| CPOP025 | −19 | −16 |
| CPOP028 | −6 | >−5 |
| CPOP031 | −11 | >−5 |
| CPOP032 | −13 | −7 |
| CPOP034 | −6 | >−5 |
| CPOP035 | −12 | −10 |
| CPOP037 | −6 | >−5 |
| CPOP038 | −6 | >−5 |
| CPOP043 | −8 | −6 |
| CPOP045 | −15 | >−5 |
| CPOP046 | −6 | >−5 |

The patient recoveries shown in FIG. 11 show an intuitive representation of recovery with patients being below the recovery norm—and observation shows that the degree of complication broadly reflects the distance below the line. Independent end-point and intermediate measures of recovery are directly provided by CPOPs.

The temporal evolution of patient pathway scores during recovery is also useful: The temporal evolution provides indications along the recovery path as to whether a patient is recovering along the nomogram or is showing the onset of complications.

Figure 12:
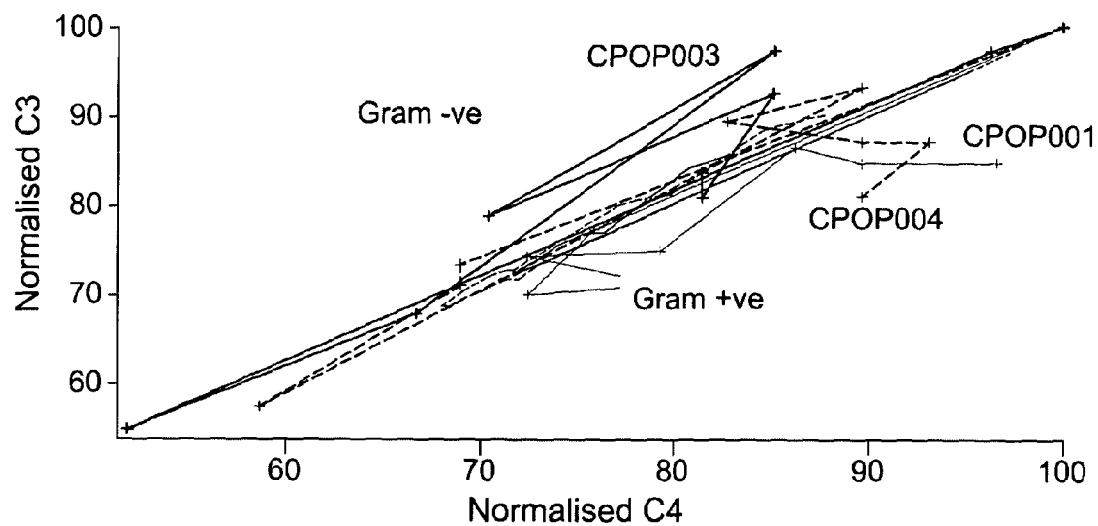
FIG. 12 illustrates differential diagnosis based on differential C-activation for three example patients (CPOP001, 003 and 004) exhibiting differential activation of CC pathways.

Differential C activation of the Alternative, Classical and Lectin pathways also provides information on the differential diagnosis of secondary infections, in particular bacterial infections. This is illustrated in FIG. 12, which shows differential diagnosis based on normalised C3 and C4 levels.

Patient Stratification may be achieved by:
Taking an early-time recovery parameter such as time to C3 min, or C3 min
Correlating this time with an end-point measure and/or a measure of complications Some or all of the measures derived from the nomograms and differential diagnosis plots can contribute to stratification of patients: Differential recovery management focussed at the strata can enhance patient recovery.

Table 6, below, lists examples of pathway metrics which may be employed in embodiments of the above described methods, and the outcomes to which they relate (which include predicted stratification; predicted clinical endpoint; and so forth). The invention contemplates that one or more (or any combination) of the metrics and correlations identified in each row of Table 6 may be employed independently to predict an outcome; and where multiple correlation parameters are listed within a single row one or more of these may be employed either alone or in combination.

TABLE 6

Metrics, correlations, and endpoints (predictions/outcomes)

| Metric | Correlation(s) | Prediction/outcome |
|---|---|---|
| Age | C3 min, C4 min, time to minima, time profiles, C3 and C4 scores | Stratification Marker |
| Gender | | Stratification Marker |
| Length of Stay | C3 and C4 scores | Proxy for well-being and recovery |
| Duration of Surgery | C3 min, C4 min, time to minima, time profiles, C3 and C4 scores | |
| C3 Minimum | CRP_max, CRP_production rate, Duration of Surgery, All pathway metrics | Stratification Marker defined by early time classes |
| C4 Minimum | CRP_max, CRP_production rate, Duration of Surgery, All pathway metrics | Stratification Marker defined by early time classes |
| Time to C3 minimum | Duration of surgery, Length of stay, C_pathscores Defining strata | Stratification Marker defined by early time classes |
| Time to C4 minimum | Duration of surgery, Length of stay, C_pathscores Defining strata | Stratification Marker defined by early time classes |
| C3 and C4 at t = 10 hrs | C_pathscores, Evolving strata | Stratification Marker |
| C3 and C4 at t = 20 hrs | C_pathscores, Evolving strata | Stratification Marker |
| C3 and C4 at t = 50 hrs | C_pathscores, Evolving strata | Potential Clinical Endpoint Internal End-point |
| C3 and C4 Pathscores(t) | C3 or C4_min (stratum) | Internal endpoint complications diagnostic |
| C2, C3, C4, C5 rate of synthesis | C_pathway scores, CRP rate of production | Liver function marker |
| CRP Level at 150 mg L$^{-1}$ | Duration of Surgery, C_pathscores | Clinical Endpoint Existing discharge condition |
| Decreasing CRP Concentration | C_pathscores, Evolving strata | Clinical Endpoint Existing discharge condition |
| CRP max | C3 and C4 scores(time), C3 at t = 10, 20, 30 | Internal End-point |
| Time to CRP Max | | Stratification Marker post hoc |
| Maximum CRP rate of production | Rate of C3 and C4 production | Liver function marker |
| Fragment eg C3dg maximum | | |
| Time to fragment maximum (depending on origin of fragment) | C3 consumption and not C4 | Differential Diagnosis marker |
| Fragment production | Alternative, Classical, Lectin or Lytic Pathway activation | |
| Medical Observations | | General System Health and Standard Tests |
| Temperature | C_depletion, C_fragment increases | Fever is correlated with infection |
| Blood Cell Counts | | |
| White Blood Cells | C_depletion, C_pathscores, C_fragment maxima, Pathway metrics | Inceased Cellular immune response |
| Neutrophils | C_depletion, C_pathscores, C_fragment maxima, Pathway metrics | Infection specificities |

Complement Fragment Analysis

It is important to establish the C3 and C4 consumption as activation of C as opposed to dilution from fluid intervention or blood loss—although either will lead to a compromised immune system. One option to address this is to detect one or more CC fragments.

Further, monitoring the level of a CC fragment has the advantage that the data is more intuitive in that the level of a fragment, say a C3 fragment such as C3dg, will generally rise in response to the severity of infection, which is easier to detect than, say, a percentage fall in the value of a normalised C protein.

Figure 13:
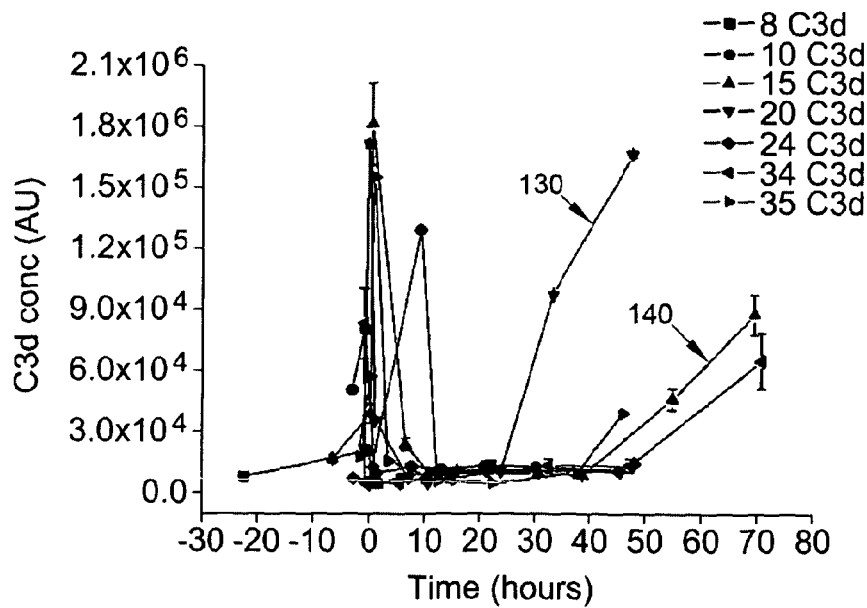
FIG. 13 shows a set of curves of CC fragment levels for set of patients, illustrating the use of a fragment level to detect complications.

Thus, referring to FIG. 13, this shows a set of curves of CC fragment levels for set of patients, illustrating the use of a fragment level, in this example C3d, to detect complications. Point X shows the initial CC response spike to the surgical insult (the slightly offset-in-time peak is probably an error in sample acquisition timing). Then, over a period of order 10 hours, the fragment level decreases (as it is cleared by the kidneys).

Curve 130 shows a patient in which after a period (20-30 hours) the consumption of C3 started to increase, resulting in a falling complement (C3) level (not shown) and a rising complement fragment (C3d) level. For this patient this indicated a complication in the surgical outcome. Curve 140 illustrates another, similar example where the increase in complement fragment level (at about 35 hours) was accompanied by increased complement (C3) consumption and, in this patient's case, very serious complications. Thus, broadly speaking, after an initial spike complications may be inferred from a secondary rise in the level of a complement fragment above a threshold. Such a measure may optionally be combined with a measure of a complement level, such as a C3 level, for example time to a minimum level (in this example a C3 minimum): if this is greater than a threshold duration, say 10 hours, again complications may be predicted. The invention contemplates that such techniques may be employed independently of the recovery pathway-based approach described above.

Fragment concentrations are typically low in the blood so changes away from a low baseline showing 10-100-fold increase is an ideal characteristic for C activation. Differentially fragments from the Alternative, Classical and Lectin pathways will show immediate differential activation and the rates of change in the fragments concentrations increasing, analysed with the rates of change of decreasing C proteins at the top of the pathways such as C3, C4, C2 produces the differential fluxes in the pathways $J_A$, $J_C$, and $J_L$. Once determined the differential diagnosis presented above is quantified.

Examples of applications of the above-described techniques include, but are not limited to: Detection age-related macular degeneration and/or atypical haemolytic uremic syndrome (detection of the CC via, for example, a FH-CRP interaction). Early prediction of the outcome of colorectal surgery—this is important because colorectal surgery is associated with overall complication rates of more than 30% and a perioperative mortality of 3-4%. Accurate prediction of/a diagnostic test for an anastomotic leak at an early stage—anastomotic leaks occur with a frequency of up to 23%. In roughly half of patients, anastomotic leaks are clinically silent and may first become evident after a median of 8 days, often when patients have developed critical illness.

Further examples of applications of the above-described techniques include, but are not limited to, determining an early or pre-symptomatic diagnosis and/or prognosis for acute and chronic diseases including: Alzheimer's disease, Multiple Sclerosis, stroke, age related macular degeneration, asthma, myocardial infarction, Crohn's disease, rheumatoid arthritis, and sepsis. Embodiments of the methods may also be used to monitor or predict the response of a damaged immune system, for example in a patient with leukemia.

Broadly speaking we have described a system/method for predicting the outcome of a medical procedure on a patient. The system/method uses using complement cascade data representing levels of a set of complement cascade markers in the patient at a succession of peri-operative time intervals, determining deviations from a mathematical model of the response to provide a pre-symptomatic prediction of the outcome. In embodiments the complement cascade pathways include the lytic pathway and at least one of the lectin pathway, the classical pathway and the alternative pathway, and the biomarkers include at least C3. The system may include an electroluminescence-based (for example from MCD LLC) or a plasmon resonance-based multianalyte detector to analyse a blood sample from the patient.

No doubt many other effective alternatives will occur to the skilled person. It will be understood that the invention is not limited to the described embodiments and encompasses modifications apparent to those skilled in the art lying within the spirit and scope of the claims appended hereto.

The invention claimed is:

1. A measuring system for determining infection in a patient who has undergone elective colorectal surgery, the system comprising:

a plasmon resonance-based biosensor array for plasmon resonance-based sensing of a plurality of different biological targets simultaneously, the plasmon resonance-based biosensor array comprising a transparent substrate having a surface bearing a plurality of assay spots, a system to flow a sample of bodily fluid of 200 µl or less over the biosensor array;

an illumination system to illuminate the biosensor array such that total internal reflection of light at a wavelength at or near a plasmon resonance results in dark-field scattered light modulated by binding of the biological targets, an image sensor to capture an image of the dark-field scattered light from the biosensor array, a processor, coupled to the image sensor, to working memory, and to program memory storing control code to process image data from the image sensor such that data from the plurality of different biological targets is acquired within a time duration of less than 60 minutes; and a user interface;

wherein the control code further comprises code to:

process the image data to determine patient complement cascade data from the sensed plurality of different biological targets, the complement cascade data comprising data representing levels of a set of complement cascade markers in the patient at a succession of time intervals following the surgery, wherein the patient complement cascade data defines a patient recovery pathway representing an evolution over time of a complement cascade in the patient, and wherein the set of complement cascade markers comprises at least proteins C3 and C4 and one or more complement fragment biomarkers derived therefrom;

compensate for dilution of levels of the complement cascade markers using at least one of the complement fragment biomarkers;

compensate levels of the complement cascade markers for a background or pre-existing activation of the complement cascade in the patient;

repeatedly measure levels of the set of complement cascade markers over time to define a set of at least two curves representing evolution over time of levels of the proteins C3 and C4 or complement fragment biomarkers derived therefrom;

determine whether the patient is infected by comparing a fit of the at least two curves to corresponding curves representing an evolution over time of a complement cascade in a plurality of patients; and output a result of the comparing to the user interface to enable a user to determine infection in a patient who has undergone elective colorectal surgery.

2. The measuring system of claim 1, wherein the program memory further stores model data defining a model comprising a representation of fluxes of complement components on the complement cascade; wherein the complement cascade include at least two of a lectin pathway, a classical pathway and an alternative pathway; wherein the output includes data defining one or more different types of infection activating the lectin pathway, the classical pathway and the alternative pathway to different degrees; wherein the processor control code is configured to determine probability data for the different types of infection dependent on fluxes of complement components for the lectin, classical and alternative pathways; wherein the fluxes comprise at least two of $J_A$, $J_C$, and $J_L$, representing the fluxes in, respectively, the alternative, classical and lectin pathways; and wherein the processor control code is configured to determine the probability data for the different types of infection dependent on a determination of one or more of:

$$J_A+J_L>J_C$$

$$J_A>J_L+J_C$$

$$J_{A'}>J_C+J_L$$

$$J_A+J_L>J_C$$

$$J_C>J_A+J_L.$$

3. The measuring system of claim 1, wherein the code to determine whether the patient is infected comprises code to determine a score evaluating the fit of the at least two curves to corresponding curves representing an evolution over time of a complement cascade in a plurality of patients; code to automatically determine whether or not the patient is infected from the score from each of the two at least curves; and code to output a result of the automatic determining to the user interface to enable the user to determine infection in a patient who has undergone elective colorectal surgery.

4. A method of determining infection in a patient who has undergone elective colorectal surgery, the method comprising:

conducting plasmon resonance-based sensing of a plurality of different biological targets simultaneously, using a plasmon resonance-based biosensor array, the plasmon resonance-based biosensor array comprising a transparent substrate having a surface bearing a plurality of assay spots;

flowing a sample of bodily fluid of 200 µl or less over the plasmon resonance-based biosensor array;

illuminating, using an illumination system, the biosensor array such that total internal reflection of light at a wavelength at or near a plasmon resonance results in dark-field scattered light modulated by binding of the biological targets;

capturing, using an image sensor, an image of a dark-field scattered light from the biosensor array;

processing image data from the image sensor such that data from the plurality of different biological targets is acquired within a time duration of less than 60 minutes;

processing the image data to determine patient complement cascade data from the sensed plurality of different biological targets, the complement cascade data comprising data representing levels of a set of complement cascade markers in the patient at a succession of time intervals following the surgery, wherein the patient complement cascade data defines a patient recovery pathway representing an evolution over time of a complement cascade in the patient, and wherein the set of complement cascade markers comprises at least proteins C3 and C4 and one or more complement fragment biomarkers derived therefrom;

compensating for dilution of levels of the complement cascade markers using at least one of the complement fragment biomarkers;

compensating levels of the complement cascade markers for a background or pre-existing activation of the complement cascade in the patient;

repeatedly measuring levels of the set of complement cascade markers over time to define a set of at least two curves representing evolution over time of levels of the proteins C3 and C4 or complement fragment biomarkers derived therefrom;

comparing a fit of the at least two curves to corresponding curves representing an evolution over time of a complement cascade in a plurality of patients to determine whether the patient is infected; and outputting a result of the comparing to a user interface to enable a user to determine infection in the patient who has undergone elective colorectal surgery.

5. The method of claim 4, wherein the determining of whether the patient is infected comprises determining a score evaluating the fit of the at least two curves to corresponding curves representing an evolution over time of a complement cascade in a plurality of patients; and automatically determining whether or not the patient is infected from the score from each of the two at least curves; the method further comprising outputting a result of the automatic determining to the user interface to enable the user to determine infection in a patient who has undergone elective colorectal surgery.

6. The method of claim 4, wherein the result enables the user to distinguish between one or more of: a Gram-positive bacterial infection, a Gram-negative bacterial infection, a viral infection, and a fungal infection.

7. An article of manufacture including a non-transitory, tangible computer readable storage medium having instructions stored thereon that, in response to execution by a computer-based system, cause the computer-based system to perform operations comprising:

conducting plasmon resonance-based sensing of a plurality of different biological targets simultaneously, using a plasmon resonance-based biosensor array, the plasmon resonance-based biosensor array comprising a transparent substrate having a surface bearing a plurality of assay spots;

flowing a sample of bodily fluid of 200 µl or less over the plasmon resonance-based biosensor array;

illuminating, using an illumination system, the biosensor array such that total internal reflection of light at a wavelength at or near a plasmon resonance results in dark-field scattered light modulated by binding of the biological targets;

capturing, using an image sensor, an image of a dark-field scattered light from the biosensor array;

processing image data from the image sensor such that data from the plurality of different biological targets is acquired within a time duration of less than 60 minutes;

processing the image data to determine patient complement cascade data from the sensed plurality of different biological targets, the complement cascade data comprising data representing levels of a set of complement cascade markers in the patient at a succession of time intervals following the surgery, wherein the patient complement cascade data defines a patient recovery pathway representing an evolution over time of a complement cascade in the patient, and wherein the set of complement cascade markers comprises at least proteins C3 and C4 and one or more complement fragment biomarkers derived therefrom;

compensating for dilution of levels of the complement cascade markers using at least one of the complement fragment biomarkers;

compensating levels of the complement cascade markers for a background or pre-existing activation of the complement cascade in the patient;

repeatedly measuring levels of the set of complement cascade markers over time to define a set of at least two curves representing evolution over time of levels of the proteins C3 and C4 or complement fragment biomarkers derived therefrom;

comparing a fit of the at least two curves to corresponding curves representing an evolution over time of a complement cascade in a plurality of patients to determine whether the patient is infected; and outputting a result of the comparing to a user interface to enable a user to determine infection in the patient who has undergone elective colorectal surgery.

* * * * *